(12) United States Patent
Hirata et al.

(10) Patent No.: US 8,258,785 B2
(45) Date of Patent: Sep. 4, 2012

(54) MAGNETIC RESONANCE IMAGING APPARATUS AND MAGNETIC RESONANCE SPECTROSCOPIC IMAGE COMPUTING METHOD

(75) Inventors: Satoshi Hirata, Kodaira (JP); Yoshitaka Bito, Kokubunji (JP); Kiyoharu Tanaka, Iruma (JP)

(73) Assignee: Hitachi Medical Corporation, Tokyo (JP)

( * ) Notice: Subject to any disclaimer, the term of this patent is extended or adjusted under 35 U.S.C. 154(b) by 495 days.

(21) Appl. No.: 12/523,259

(22) PCT Filed: Dec. 17, 2007

(86) PCT No.: PCT/JP2007/074205
§ 371 (c)(1),
(2), (4) Date: Jul. 15, 2009

(87) PCT Pub. No.: WO2008/087822
PCT Pub. Date: Jul. 24, 2008

(65) Prior Publication Data
US 2010/0013481 A1 Jan. 21, 2010

(30) Foreign Application Priority Data
Jan. 17, 2007 (JP) .................................. 2007-008008

(51) Int. Cl.
*G01V 3/00* (2006.01)
(52) U.S. Cl. ......................... 324/307; 324/309; 324/312
(58) Field of Classification Search .................. 324/307, 324/309, 312
See application file for complete search history.

(56) References Cited

U.S. PATENT DOCUMENTS

| 5,879,299 A * | 3/1999 | Posse et al. ................... 600/410 |
| 6,995,560 B2 * | 2/2006 | Duerk et al. .................. 324/310 |
| 7,298,144 B2 * | 11/2007 | Reeder et al. ................. 324/307 |
| 7,664,541 B2 * | 2/2010 | Wang et al. ................... 600/410 |
| 2006/0139027 A1 | 6/2006 | Dreher et al. |

FOREIGN PATENT DOCUMENTS

| JP | 11-076191 | 3/1999 |
| JP | 2001-346779 | 12/2001 |
| JP | 2002-315732 | 10/2002 |

* cited by examiner

*Primary Examiner* — Louis Arana
(74) *Attorney, Agent, or Firm* — Antonelli, Terry, Stout & Kraus, LLP.

(57) ABSTRACT

An object of the invention is to obtain a magnetic resonance spectroscopic image to which the MAC summation is applied with high accuracy and in short time, even though a phase characteristic distribution of the MAC has a spatial non-uniformity, in the MRSI measurement using a magnetic resonance imaging apparatus provided with a MAC. Using a non-water-suppressed image signal with high SNR, obtained in the non-water-suppressed measurement (a reference measurement) without water suppression, a correction value for correcting the phase distortion for the MAC summation is calculated on each pixel in each coil. After correcting a phase on each pixel in each coil of a main-scan image signal measured under suppressing water (water-suppressed image signal) using the corrective value, signal adding operation (summation) is performed. Then, a phase correction in a spectrum-axis is to be performed on the summed spectrum signal.

15 Claims, 10 Drawing Sheets

First example
(using a procedure
shown in FIG. 6)

Second example
(using a procedure
shown in FIG. 8)

MAGNETIC RESONANCE IMAGING APPARATUS AND MAGNETIC RESONANCE SPECTROSCOPIC IMAGE COMPUTING METHOD

TECHNICAL FIELD

The present invention relates to a magnetic resonance imaging technology, or more particularly to an apparatus and a method suitable for obtaining of a magnetic resonance spectroscopic image.

BACKGROUND ART

A magnetic resonance imaging apparatus irradiates a radiofrequency magnetic field at specific frequency to a subject placed in a static magnetic field, so as to excite nuclear magnetization of each nucleus of hydrogen or the like contained in the subject and to detect a magnetic resonance signal generated from the subject and thereby acquiring physical/chemical information. In addition to a magnetic resonance imaging (hereinafter abbreviated as MRI) now in widespread use, a magnetic resonance spectroscopic imaging (herein after abbreviated MRSI), which separates magnetic resonance signals to be rendered as images every molecules with a base as to the difference (hereinafter called chemical shift) among resonant frequencies due to the difference among chemical bonds of various molecules including a hydrogen nucleus, is known as a method of imaging using the magnetic resonance imaging apparatus.

By using MRSI, a distribution of metabolite in vivo can be imaged non-invasively. However, a concentration of each metabolite is often very low so that the signal to noise ratio (hereinafter, called SNR) becomes low. Therefore, it is difficult to improve spatial resolution and time resolution. When a signal is measured without water suppression of high concentration upon execution of a MRSI measurement, a weak signal of a metabolite is buried in a skirt of a very strong signal peak generated from water. This makes it difficult to separate and extract a metabolite signal and therefore, a pre-processing for suppressing water signal is performed immediately before execution of usual excitation and detection. The measurement in which the MRSI measurement is performed after a pre-processing for suppressing water signal is called a water-suppressed measurement.

In the MRSI, it is necessary to perform a process called a phase correction in a spectrum-axis direction for calculating image information reflecting concentrations of various metabolites contained in vivo. In the phase correction in the spectrum-axis direction, spectrum signals having chemical shift information are made in phase, where, the spectrum signal is obtained by performing a transformation between a time-component and a frequency-component in a time-axis direction (for example, a Fourier transform), on measured magnetic resonance signal. However, in the MRSI, a low SNR, in measuring metabolite, makes SNR of signals acquired by the water-suppressed measurement low. That results in reducing the phase correction accuracy. There is a technique where, the phase correction in the spectrum-axis direction on a spectrum with low SNR obtained by the water-suppressed measurement is performed, using a phase characteristic calculated from a spectrum with high SNR obtained in the MRSI measurement without a pre-processing for suppressing a water signal (non-water-suppressed measurement) (refer to, a patent document 1 for example).

On the other hand, there is a technique in the recent MRI where an image measurement is performed, using a multi-array coil (MAC), combined multiple surface coils each having a high receiving sensitivity flatly or spatially. Using the MAC, images with high SNR can be obtained by summing obtained multiple images. Also in the MRSI measurement, it is expected to improve the SNR with a usage of the MAC.

Patent document 1
  Japanese patent application laid open No. 2001-346779

DISCLOSURE OF THE INVENTION

Problem to be Solved by the Invention

A magnetic resonance signal (called a sequential data or a RAW data) measured in the MRI includes a real part (Real component) and an imaginary part (Imaginary component). There are several ways for a MAC summation (methods of summing multiple images), such as, (A) a method of simply adding imaging signals acquired in each coil (addition of each real part and addition of each imaginary part) (B) a method of adding the square root of square-sum of imaging signals (the real part×the real part+the imaginary part×the imaginary part) acquired in each coil. (C) a method of adding an image signals acquired in each coil, for each real part and for each imaginary part, respectively, after correcting a phase thereof.

Regarding each method of (A) to (C) as mentioned above, according to the method of (A), although only the real part or the imaginary part can be extracted from a summed spectrum, a summation effect (SNR improving effect) will be degraded if a phase distribution of each coil has a spatial non-uniformity. According to the method of (B), although the summation effect (SNR improving effect) will not be degraded, even the phase distribution has a spatial non-uniformity, the real part and the imaginary part cannot be extracted separately from the summed spectrum. According to the method of (C), only the real part or the imaginary part can be extracted from the summed spectrum, also, summation effect (SNR improving effect) will not be degraded if the SNR of obtained signal is high, even though a phase distribution has a spatial non-uniformity.

When analyzing a spectrum, it is necessary to extract only the real part of the spectrum after applying the MAC summation due to the necessity of displaying only the real part of the spectrum after applying the MAC summation. Therefore, the method (C) which satisfies this requirement and keeps summation effect even a phase distribution has a spatial non-uniformity, has an advantage in the MAC summation in the MRSI. However, even using the method of (C), since a concentration of the metabolite in vivo is very low in the MRSI measurement, there are cases that the SNR obtained by the water-suppressed measurement becomes very low, a correcting accuracy of the phase correction may be reduced. In addition, since a computational amount of the method of (C) shall increase in proportion to the number of coils, the operation time will be prolonged.

The present invention has been made in view of the situation above, and an object of the invention is to obtain a magnetic resonance spectroscopic image to which the MAC summation is applied with high accuracy and in short time, even though a phase characteristic distribution of the MAC has a spatial non-uniformity, in the MRSI measurement using a magnetic resonance imaging apparatus provided with a MAC.

Means to Solve the Problem

The present invention provides an improved computational algorithm of the methods of (C). According to the present invention, using a non-water-suppressed image signal with high SNR, obtained in the non-water-suppressed measurement (reference measurement) without water suppression, a correction value for correcting the phase distortion for the MAC summation is calculated pixel by pixel and coil by coil. After making main-scan image signals measured under suppressing water (water-suppressed image signal) in phase for each pixel in each coil using the corrective value, signal adding operation (summation) is performed. Then, a phase correction in a spectrum-axis is to be performed on the summed spectrum signal.

A measurement time can also be reduced by reducing a repetition time and the number of repetition of a measurement at the reference measurement.

Conventionally, when summing signals acquired at each coil, an equivalent summation with weighting coefficient 1 thereto is performed. However, in the present invention, a SNR of each pixel and of each coil is calculated on an image signal acquired in the reference measurement in advance, and when summing main-scan signals, a summation is performed after multiplying a coefficient calculated from the SNR of each pixel of each coil to the main-scan signals.

Specifically, the present invention provides a magnetic resonance imaging apparatus comprising, a magnetic field generating means for generating a static magnetic field, a radiofrequency magnetic field and a gradient magnetic field respectively, a detecting means for detecting a magnetic resonance signal generated from a subject placed in the static magnetic field, a measurement control means for controlling the magnetic field generating means and the detecting means, and a computing means for reconstructing a magnetic resonance spectroscopic image using a nuclear magnetic resonance signal so as to display, where, the detecting means comprises a receiving coil being made up of a multiple element coils; wherein, the measurement control means comprises, a first measurement sequence means for performing a first measurement sequence for measuring a nuclear magnetic resonance spectrum without suppressing a nuclear magnetic resonance signal from water and a second measurement sequence means for performing a second measurement sequence for measuring a nuclear magnetic resonance spectrum with suppressing a nuclear magnetic resonance signal from water, and, the computing means calculates a signal phase value of each pixel of each of the multiple element coils using the nuclear magnetic resonance signal of each pixel measured at each of the multiple element coils in the first measurement sequence means, and performs a phase correction for each nuclear magnetic resonance signal of each pixel measured at each of the multiple element coils in the second measurement sequence means using the signal phase value above-mentioned so as to summed images reconstructed for each of the multiple element coils.

The present invention further provides a method for calculating a magnetic resonance spectroscopic image from a magnetic resonance signal obtained by irradiating a radiofrequency magnetic field to a subject placed in a static magnetic field at least once, applying a gradient magnetic field to the subject at least once after the irradiation of the radiofrequency magnetic field, and detecting the magnetic resonance signal generated from the subject at a receiving coil after the application of the gradient magnetic field I, wherein, the receiving coil is a multi-array coil (MAC) being made up of the multiple element coils $L(i)$ (here, i denotes an integer from 1 to I: $i=1, 2, \ldots I$, representing a coil number), and the method comprising, a first measuring step for measuring a spectral information of a 2-dimensional k-space or a 3-dimensional k-space $(kx(a), ky(b), kz(c))$ (where "a" represents measurement number in a kx-axis direction of an integer "A" or less, "b" represents measurement number in a ky-axis direction of an integer "B" or less, and "c" represents measurement number in a kz-axis direction of an integer "C" or less; in case 2-dimensional measurement, any one of "A", "B", and "C" is 1 and rest of two are integers of 2 or more, and in case 3-dimensional measurement, all of "A", "B", and "C" are integers of 2 or more) under non-water-suppressed condition, a first k-space and real-space transform step for performing a transform between a k-space component and a real-space component in each k-space axis (kx, ky kz) direction on a magnetic resonance signal $Sw1(L(i))(kx(a), ky(b), kz(c))(t(j))$ (where, "j" is an integer "J" or less representing a data number in time-axis (t-axis) direction) acquired at each element coil in the first measurement step so as to calculate a magnetic resonance signal in a 2-dimensional real-space or a 3-dimensional real-space $(x(a), y(b), z(c))$, a phase value calculating step for calculating a phase value $\Phi w(L(i))(x(a), y(b), z(c))(t(N))$ of a "N"th signal $Sw2(L(i))(x(a), y(b), z(c))(t(N))$ from the top for each real-space point of each element coil, as for the magnetic resonance signal $Sw2(L(i))(x(a), y(b), z(c))(t(j))$ of the real-space calculated in the first k-space and real-space transform step so as to obtain a correction value from the calculation result, a second measurement step for measuring a spectral information of the 2-dimensional k-space or the 3-dimensional k-space $(kx(a), ky(b), kz(c))$ under water-suppressed condition, a second k-space and real-space transform step for performing a transform between a k-space component and a real-space component, in each k-space axis direction, on a k-space magnetic resonance signal $Sm1(L(i))(kx(a), ky(b), kz(c))(t(j))$ acquired at the each element coil in the second measurement step so as to calculate a magnetic resonance signal in the 2-dimensional real-space or the 3-dimensional real-space $(x(a), y(b), z(c))$, a phase value correction step for performing a phase correction, where the phase values $\Phi m(L(i))(x(a), y(b), z(c))(t(j))$ of all the points are corrected point-by-point of each real-space point of each element coil, using the correction value calculated in the phase value calculating step, on the magnetic resonance signal $Sm2(L(i))(x(a), y(b), z(c))(t(j))$ acquired in the second k-space and real-space transform step so as to calculate a phase corrected magnetic resonance signal $Sm3(L(i))(x(a), y(b), z(c))(t(j))$, a MAC summation step for subjecting to a complex addition of the magnetic resonance signal $Sm3(L(i))(x(a), y(b), z(c))(t(j))$ of each real-space point of each element coil calculated in the phase value correction step, for each real-space point so as to make an added signal value $Sm4(x(a), y(b), z(c))(t(j))$ as a magnetic resonance signal value (a magnetic resonance signal value after the MAC summation) applied the MAC summation, where multiple images obtained by the MAC are added to each other, a time and frequency transform step for performing a transform between a time component and a frequency component in a time-axis direction on a magnetic resonance signal value $Sm4(x(a), y(b), z(c))(t(j))$, which is a signal value of each real-space point of the magnetic resonance signal value after the MAC summation, calculated in the MAC summation step so as to calculate a magnetic resonance spectroscopic image $Sm5(x(a), y(b), z(c))(f(j))$ of the 2-dimensional real-space or the 3-dimensional real-space having information in a frequency axis (f-axis) direction.

Effect of the Invention

According to the present invention, in a MRSI measurement using a magnetic resonance imaging apparatus provided with a MAC, it is possible to obtain a magnetic resonance spectroscopic image, to which a MAC summation is applied with high accuracy and in short time, even though phase characteristic distribution of MAC has a spatial non-uniformity.

BEST MODE FOR CARRYING OUT THE INVENTION

<First Embodiment>

The first embodiment of the present invention will be described below with reference to the drawings.

Figure 1A:
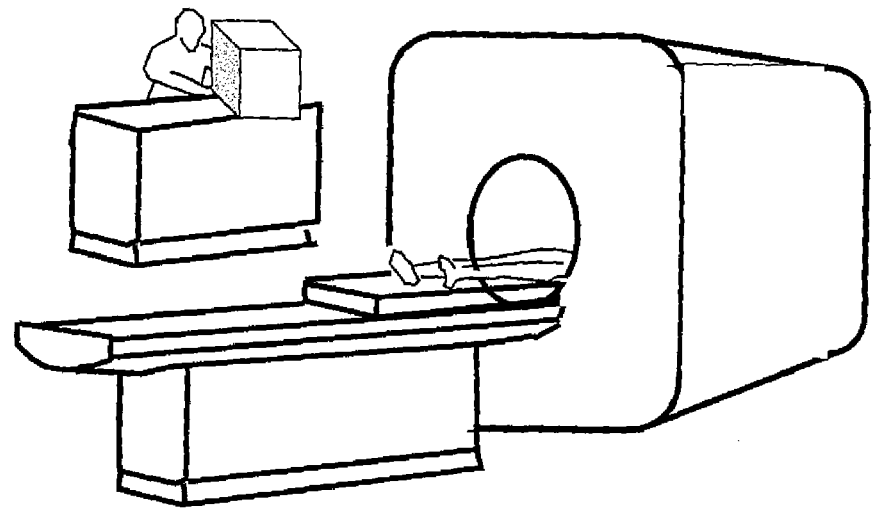
FIGS. 1A to 1C are external views illustrative of the magnetic resonance imaging apparatus according to the first embodiment.
Figure 1B:
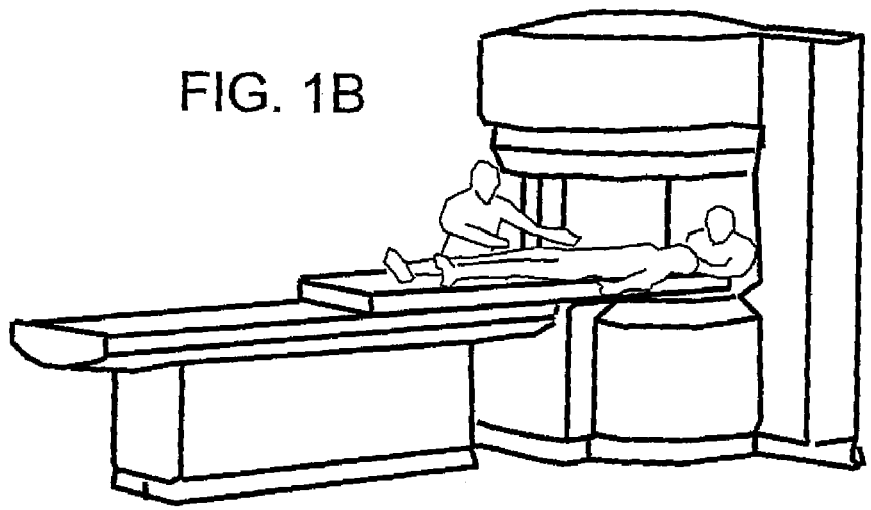
Figure 1C:
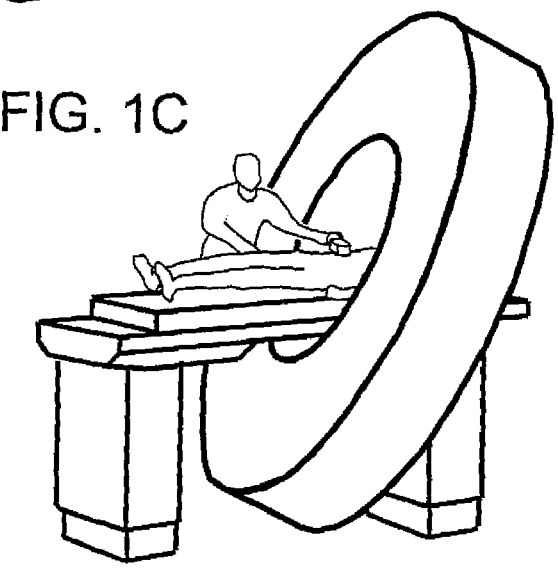

FIGS. 1A to C show the appearances of the magnetic resonance imaging apparatus of the present embodiment, respectively. FIG. 1A shows a magnetic resonance imaging apparatus of a horizontal magnetic field system that uses a tunnel type magnet which generates a static magnetic field with a solenoid coil. FIG. 1B shows a hamburger type magnetic resonance imaging apparatus of vertical magnetic field system in which magnets are separated into upper and lower sections to enhance a sense of openness. FIG. 1C shows a magnetic resonance imaging apparatus of the same tunnel type as shown in FIG. 1A, where a magnet is made short in depth and is tilted thereby to enhance a sense of openness. It is noted that the present invention may apply any type of magnetic resonance imaging apparatus known in public including these magnetic resonance imaging apparatuses.

Figure 2:
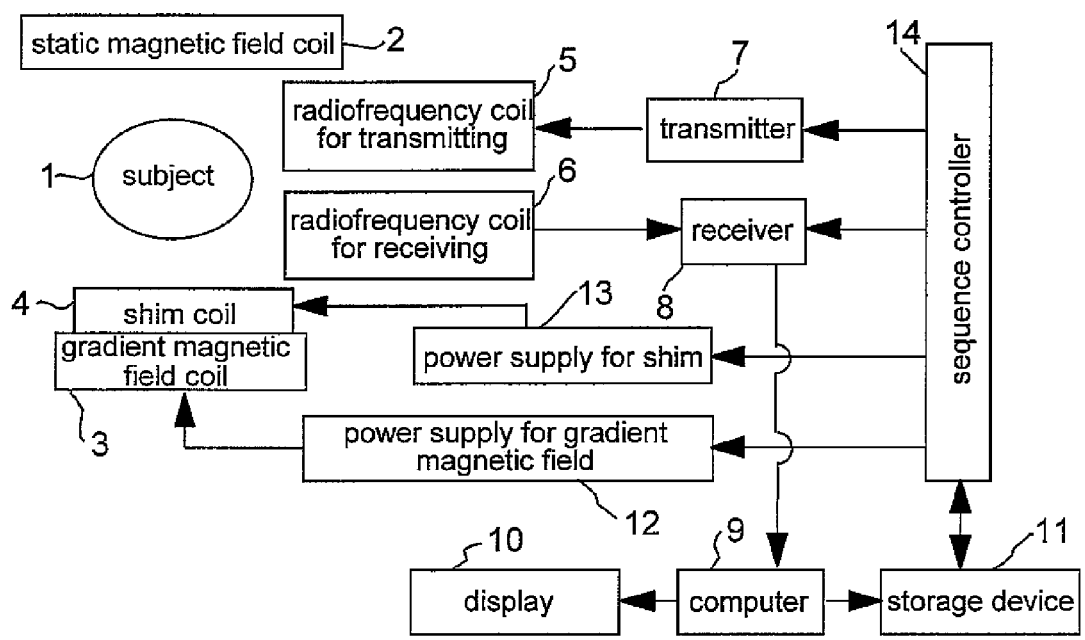
FIG. 2 is a block diagram of a confiquratibn of a magnetic resonance imaging apparatus according to the first embodiment.

FIG. 2 is a block diagram showing a configuration of a magnetic resonance imaging apparatus of the present embodiment. The magnetic resonance imaging apparatus is provided with a static magnetic field coil 2 for generating a static magnetic field in the space where a subject 1 is placed, a gradient magnetic field coil 3 for applying gradient magnetic fields in three-directions orthogonal to one another, a radiofrequency coil for transmitting 5 (hereinafter it is referred to as "transmitting coil") for irradiating a radiofrequency magnetic field to the subject 1, and a radiofrequency coil for receiving 6 (hereinafter it is referred to as "receiving coil") for receiving a magnetic resonance signal generated from the subject 1. Also it can be provided with a shim coil 4 which can adjust the uniformity of the static magnetic field.

Various types of static magnetic field coils 2 can be applied according to the configuration of the apparatus shown in FIG. 1. The gradient magnetic field coils 3 and the shim coil 4 are driven by a power supply 12 for the gradient magnetic field and a power supply 13 for the shim, respectively. The radio frequency magnetic field irradiated from the transmitting coil 5 is generated by a transmitter 7 and applied to the subject 1 placed in the static magnetic field.

Figure 3:
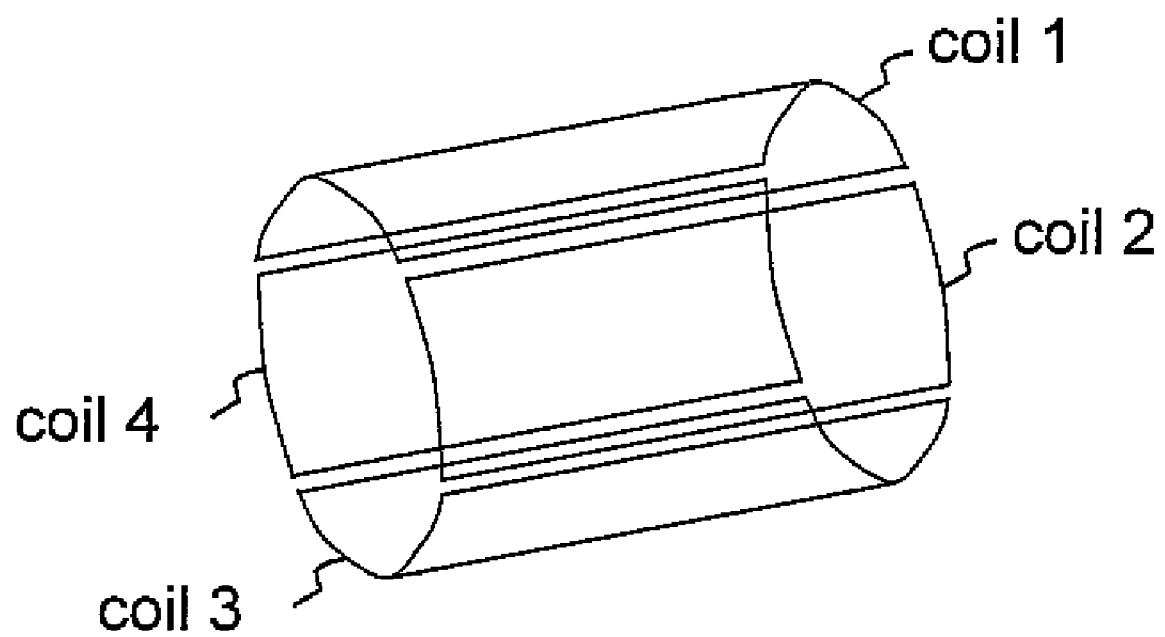
FIG. 3 shows an example of a receiving coil used in a magnetic resonance imaging apparatus according to the first embodiment.

The receiving coil 6 is made up of a multi-array coil in which multiple coils are arranged in a shape of a plane or spatially. Multi-array coils used for the MRI known in public can be applicable for the multi-array coil. FIG. 3 shows one example of the multi-array coils. The multi-array coil shown in FIG. 3, with four planar coils (coil 1, coil 2, coil 3 and coil 4) being arranged cylindrically, has a resonance property tuned on a resonant frequency of a nucleus of a measurement target. This resonant circuit is configured as a combination of a condenser with capacitance "C" and a coil with inductance "L", both of which are omitted in the figure. It is possible to provide a decupling circuit for avoiding magnetic coupling among element coils, if necessary. It is noted that the receiving coil exemplified in FIG. 3 has four element coils, the number of the element coils are not limited and may be any as long as two or more.

While FIG. 2 shows a configuration in which the transmitting coil 5 and the receiving coil 6 are provided separately, a configuration also can be applicable in which one radiofrequency coil is used for both transmission and reception. In this case, the multi-array coil shown in FIG. 3 can be also used for transmission.

The magnetic resonance signal detected by the receiving coil 6 is transmitted to a computer 9 through a receiver 8. The computer 9 performs various computations on the magnetic resonance signal according to pre-stored programs or instructions from a user, so as to generate spectral information and image information. In the magnetic resonance imaging apparatus of the present embodiment, a computer 9 performs calculations of a correction value and a summation factor necessary for correction on magnetic resonance signals detected at each element coil that makes up the receiving coil 6, a MAC summation calculation, and a corrective calculation. The computer 9, to which a display 10, a storage device 11, a sequence controller 14, an input device 15, and the like are connected, displays generated spectral information and image information described above on the display 10 or stores them in the storage device 11. Input device 15 is used for inputting measurement conditions and conditions necessary for computation, and If necessary, these measurement conditions and so on are also stored in the storage device 11.

The sequence controller 14 controls the power supply 12 for the gradient magnetic field coil 3, the power supply 13 for the shim coil 4, the transmitter 7 and the receiver 9 according to pre-stored programs or instructions from a user. The time chart of the control (pulse sequence) is predetermined in accordance with methods of imaging and is stored in the storage device 11. The sequence controller 14 in the magnetic resonance imaging apparatus of the present embodiment is provided with a pulse sequence for executing a MRSI measurement without suppressing a nuclear magnetic resonance signal of water (a non-water-suppressed measurement), and a pulse sequence for executing the MRSI measurement with suppressing the nuclear magnetic resonance signal of water (a water-suppressed measurement). The sequence controller 14 performs a measurement with these two kinds of pulse sequences in combination. Public known pulse sequences are employed for these pulse sequences. An example is shown in FIG. 4 and FIG. 5.

Figure 4:
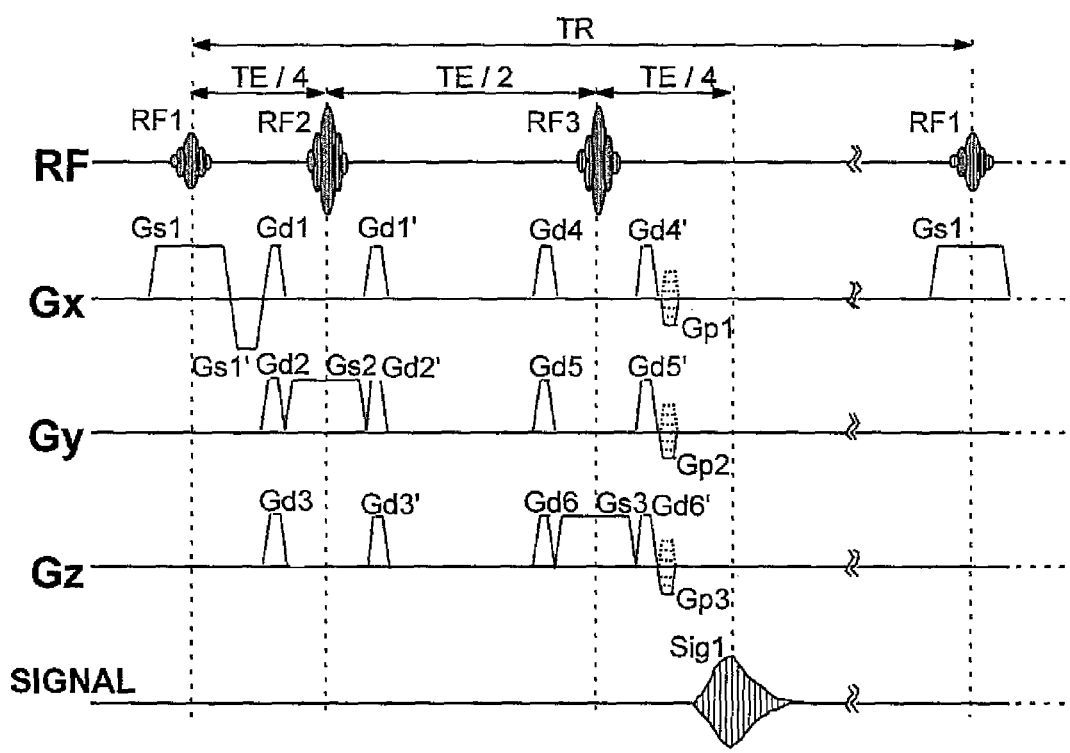
FIG. 4 illustrates an example of a pulse sequence for MRSI measurement according to the first embodiment.
Figure 5:
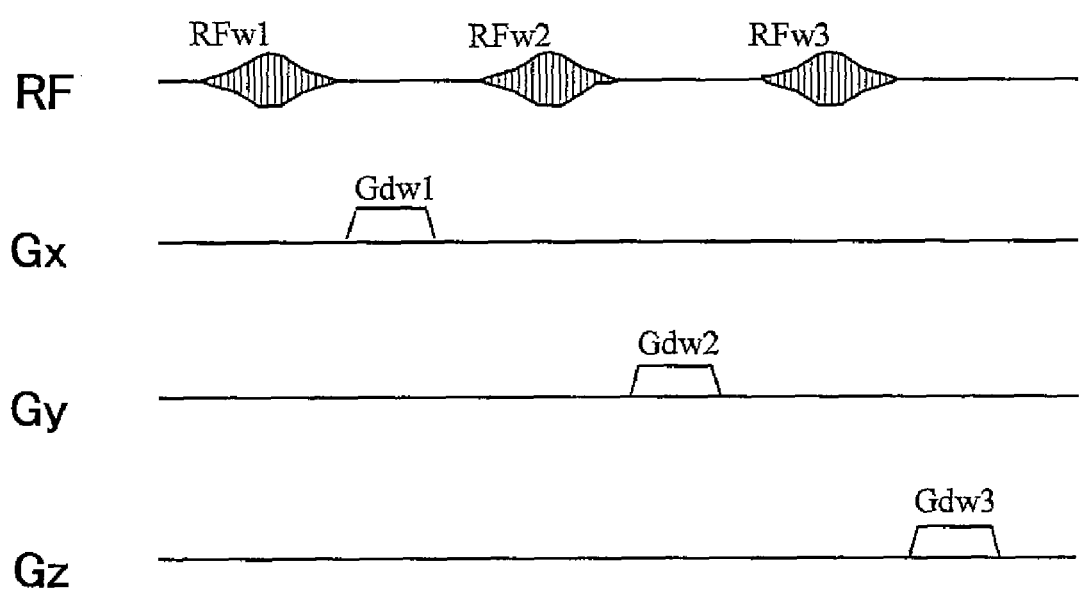
FIG. 5 illustrates an example of a pre-pulse sequence for suppressing water signal.

FIG. 4 shows an example of a pulse sequence for the MRST measurement (a MRSI pulse sequence). In the present embodiment, the MRSI pulse sequence shown in the FIG. 4 is executed for both in the non-water-suppressed measurement and in the water-suppressed measurement. FIG. 5 shows an example of a pre-pulse sequence executed prior to the water-suppressed measurement.

According to the MRSI pulse sequence, the sequence controller 14 controls as follows. First, a first gradient magnetic field (the gradient magnetic field in an x-axis direction) Gs1 for selecting a first slab (a plane area perpendicular to the x-axis) and a first radiofrequency magnetic field RF1 called a "90-degree pulse" are applied simultaneously to make nuclear magnetization in the first slab into an excitation state. Here, TE denotes an echo time and TR denotes a repetition time.

After TE/4 elapsing from the irradiation of the RF1, a second gradient magnetic field (the gradient magnetic field in an y-axis direction) Gs2 for selecting the second slab (a plane area perpendicular to the y-axis) and a second radiofrequency magnetic field RF2 called "180-degree pulse" are applied simultaneously. Thus, among the nuclear magnetization in the first slab excited by the RF1, the nuclear magnetization also in the second slab is inverted 180 degree.

After TE/2 elapsing from the irradiation of the RF2, a third gradient magnetic field (the gradient magnetic field in an z-axis direction) Gs3 for selecting a third slab (a plane area perpendicular to the z-axis) and a third radiofrequency magnetic field RF3 called "180-degree pulse", are applied simultaneously so that among the nuclear magnetization in the intersection area of the first slab and the second slab inverted by the RF2, the nuclear magnetization also in the third slab is inverted 180 degree again. With the application of the above three sets of radiofrequency magnetic fields and gradient magnetic fields, a magnetic resonance signal Sig1 is generated at an echo time, that is a point of time TE/4 elapsing from irradiation of the RF3. The generated magnetic resonance signal Sig1 is sampled "J" times at a predetermined sampling interval.

Then, while changing applying intensity of phase-encoding gradient magnetic fields Gp1, Gp2 and Gp3 providing 3-dimensional space information step-by-step, the measurement of the Sig1 is repeated.

Since the Sig 1, with variations in signal intensity in a time-axis direction, has information about a chemical shift, a magnetic resonance spectrum signal can be obtained by applying a Fourier transform in the time-axis direction thereto, as described below.

It is noted that, Gs1' applied immediately after the application of Gs1 is a gradient magnetic field for re-phase with respect to Gs1. Gd1 and Gd1', Gd2 and Gs2' and Gd3 and Gd3' applied before and after the application of RF2 are respectively gradient magnetic fields for de-phasing the nuclear magnetization excited by the irradiation of RF2 without disturbing the phase of the nuclear magnetization excited by the irradiation of RF1. Gd4 and Gd4', Gd5 and Gd5', and Gd6 and Gd6' applied before and after the application of RF3 are respectively gradient magnetic fields for de-phasing the nuclear magnetization excited by the irradiation of RF3 without disturbing the phase of the nuclear magnetization excited by the irradiation of RF1.

With the execution of the pulse sequence shown in FIG. 4, it is possible to selectively excite only the nuclear magnetization in an area (exciting area R1) where the above three slabs intersect. Repeating excitation and measurement with varying the application intensity of the phase-encoding gradient magnetic field Gp1 by "A" steps, Gp2 by "B" steps and Gp3 by "C" steps, respectively, magnetic resonance signals of "A"דB"דC" in number are detected, so as to measure a series of data for filling a measurement space (kx, ky, kz) called a frequency space (k-space).

It is noted that kx indicates an x-axis component of the k-space. Similarly, ky and kz indicate a y-axis component and a z-axis component, respectively, and "b" and "c" indicate integers "B" and "C", respectively. In a 2-dimensional k-space, any one of "A", "B" and "C" is 1 and remaining two are integers 2 or more, and in a 3-dimensional k-space, all of "A", "B" and "C" are integers 2 or more.

Next, an inverse Fourier transform, where a k-space component and a real-space component are transformed therebetween in each axis direction of k-space, is performed on magnetic resonance signals of "A"דB"דC" in number so as to obtain a magnetic resonance spectrum generated from each of spatial points of "A"דB"דC" in number.

On the other hand, in the water-suppressed measurement, the sequence controller 14 executes a pre-pulse sequence for suppressing a water signal as shown in FIG. 5 immediately before the excitation and the detection in the MRSI sequence shown in FIG. 4. That means, in the water-suppressed measurement, the pulse sequence shown in the FIG. 5 and the MRSI sequence shown in the FIG. 4 are executed as a set.

In the pre-pulse sequence, a radiofrequency magnetic field (a radiofrequency magnetic field for water excitation) RFw1, having a transmission frequency Ft set to a magnetic resonant frequency Fw of water and an excitation frequency band width ΔFt is set to a order of a wafer peak width ΔFw, is first irradiated to excite only nuclear magnetization contained in molecules of water (selective excitation of nuclear magnetizations in the water). Next, a de-phase gradient magnetic field Gdw1 is applied to differentiated the phases of nuclear magnetization contained in the water molecules placed in the excitation state from one another and to bring a vector sum of water's magnetization to zero (pseudo saturation of water magnetization). In order to further increase the effect of suppressing the water signal, the application of a radiofrequency magnetic field and a de-phase gradient magnetic field, which are similar to the radiofrequency magnetic field RFw1 for water excitation and the de-phase gradient magnetic field Gdw1, is performed several times repeatedly. FIG. 5 shows a sequence example in which the application is repeated three times, however, the number of repetitions is not limited three. Hereinafter, RFw represents all of radiofrequency magnetic fields, and Cdw represents all of gradient magnetic fields, unless they should be explained distinctively. A Gauss waveform having an excitation frequency characteristic of a narrow bandwidth is often used as the radiofrequency magnetic field RFw1. Although the example shown in FIG. 5 is of an example in which a gradient magnetic field of any one axis of Gx, Gy and Gz is applied as the de-phase gradient magnetic field, gradient magnetic fields of all three axes of Gx, Gy and Cz may be applied simultaneously. Alternatively, any two axes may be applied simultaneously. A weak signal of a metabolite is measured by executing the MRSI sequence shown in FIG. 4 while the pseudo saturation state of the water magnetization is continuing.

While the flip angle of the radiofrequency magnetic field RFw for water excitation is set to the neighborhood of 90 degree in many cases, various combinations or numerical values can be used as the applied number of axes or applying strengths as to the de-phase gradient magnetic fields Gdw.

Also, in the non-water-suppressed measurement, a pre-pulse sequence shown in the FIG. 5 can be executed, with the flip angle of the radiofrequency magnetic field RFw being set to the 0 degree, immediately before executing the MRSI sequence shown in FIG. 4. Thus, the effect of the eddy currents induced by the de-phase gradient magnetic field Gdw in the execution of the non-water-suppressed measurement can be made similar to that in the water-suppressed measurement. Specifically, both the non-water-suppressed measurement and the water-suppressed measurement are configured that the pre-pulse sequence shown in the FIG. 5 is executed prior to the MRSI sequence shown in the FIG. 4, and the flip angles of the all the radiofrequency magnetic field RFw for water excitation shown in the FIG. 5 are changed between 0 degree and 90 degree so as to switch the non-water-suppressed measurement and the water-suppressed measurement.

Since the signal of metabolite detectable in vivo tends to be very weak, measurements under the same condition (measurements without changing gradient magnetic fields for phase encode) can be repeated multiple times so as to average the obtained signals (adding up operation) for the purpose of enhancing a signal-to-noise ratio (SNR) of an obtaining spectrum.

Hereinafter, an overview of a phase correction in the MRSI will be explained. The magnetic resonance signal measured by phase detection (called a sequential data or a RAW data) includes a real part (a Real component) and an imaginary part (an Imaginary component). A signal phase $\Phi(t)$ of a magnetic resonance signal $F(t)$ at a time of "t" is defined as the following equation 1:

$$\Phi(t)=\tan^{-1}(Im(F(t))/Re(F(t))) \quad \text{(Equation 1)}$$

Where, $\tan^{-1}$ represents an arctangent function, $Im(X)$ represents the imaginary part of a complex number "X", and $Re(X)$ represents the real part of a complex number "X".

Upon performing transform operation between a time component and a frequency component (for example Fourier transform) in the time-axis direction on the magnetic resonance signal $F(t)$, a spectrum signal S including the chemical shift information is obtained. An target of the phase correction is the spectrum signal S. A signal phase $\Phi(i)$ of the "i"th data $S(i)$ of the spectrum signal S is defined as the following equation 2:

$$\Phi(i)=\tan^{-1}(Im(S(i))/Re(S(i))) \quad \text{(Equation 2)}$$

A first order component C1 and a 0 order component C0 are included in a component of a signal phase to be corrected (phase distortion) in the spectrum signal S. The first order component C1, which is a variance of a signal phase $\Phi(i)$ varying in proportion to the data number "i", is a phase distortion generated according to the amount of the chemical shift (a difference of the resonant frequency). The 0 order component C0 is an offset variance component of the signal phase c(i), independent to the data number "i". A phase distortion P(i) consisting of both of the components is defined as the following equation 3:

$$P(i)=C1 \times i + C0 \quad \text{(Equation 3)}$$

The phase correction is performed in such a manner that the phase distortion P(i) obtained by the (Equation 3) is subtracted from the signal phase $\Phi(i)$ obtained by the (Equation 2).

In the present embodiment, only the offset variance component (0 order component) of the phase distortion with largely affected is corrected at a phase correction performed before the MAC summation, and a phase correction up to the first component is performed after the MAC summation. The offset variance component (0 order component) of the phase distortion is found from the magnetic resonance imaging signal with high SNR obtained by the non-water-suppressed measurement.

Figure 6:
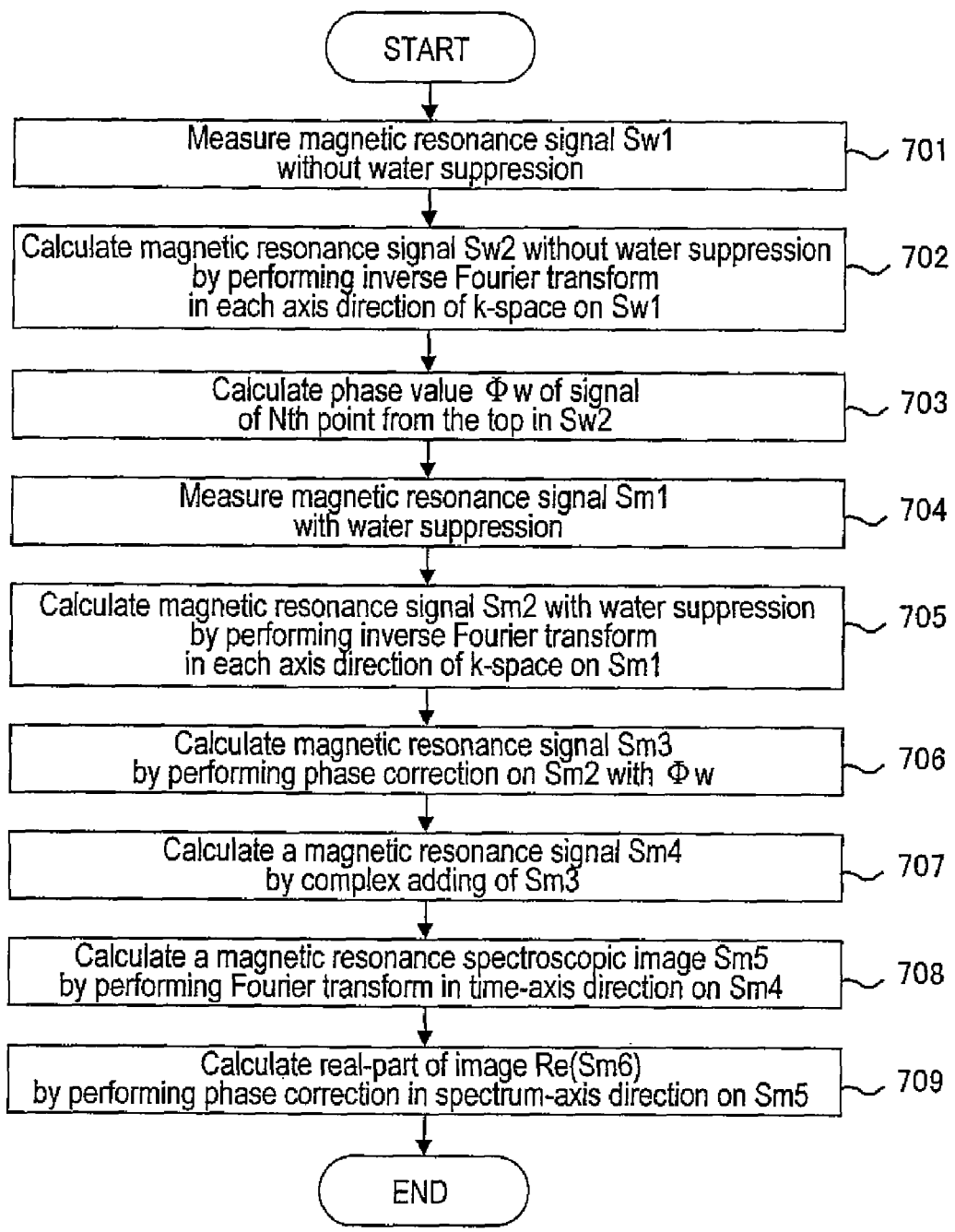
FIG. 6 is a flowchart of the measurement process according to the first embodiment.

Next, the MRSI measurement in the present embodiment will be explained. FIG. 6 shows an example of a measurement procedure of the present embodiment. In the present embodiment, the non-water-suppressed measurement (reference measurement) is performed so as to obtain the 0 order component of the phase distortion of each pixel from, or measured by, each element coil (hereinafter, also named, "each pixel of each element coil") as a phase correction value (a correction value for the MAC summation). Then, a phase of the magnetic resonance signal of each pixel of each element coil is corrected using the obtained correction value for the MAC summation, where the magnetic resonance signal is acquired through the water-suppressed measurement (main-scan), and the MAC summation is performed. After the MAC summation, the phase correction in a spectrum-axis direction is performed on the magnetic resonance signal of each pixel. In each of the following steps, the sequence controller 14 takes in charge of controlling sequences and the computer 9, processing the obtained data.

First, the non-water-suppressed measurement mentioned above is executed using a receiving coil being made up of multiple element coils L(i) (where, "i" is an integer from 1 to I: i=1, 2, . . . I, representing a coil number) so as to obtain a spectral information of the 2-dimensional k-space or the 3-dimensional k-space (kx(a), ky(b), kz(c)) (where "a" represents measurement number in a kx-axis direction of an integer "A" or less, "b" represents measurement number in a ky-axis direction of an integer "B" or less, and "c" represents measurement number in a kz-axis direction of an integer "C" or less; in case of 2-dimensional measurement, any one of "A", "B", and "C" is 1 and rest of two are integers of 2 or more, and in case 3-dimensional measurement, all of "A", "B", and "C" are integers of 2 or more) under non-water-suppressed condition at each element coil L(i) (step 701). The obtained k-space spectral information (a magnetic resonance signal) of each element coil L(i), are denoted as Sw1(L(i))(kx(a), ky(b), kz(c))(t(j)) (where, "j" is an integer "J" or less representing a data number in time-axis (t-axis) direction).

Next, an operation for transforming between a k-space component and a real-space component (for example a inverse Fourier transform) in each axis direction of k-space (kx, ky, kz) is performed on the k-space magnetic resonance signal Sw1(L(i))(kx(a), ky(b), kz(c))(t(j)) of each element coils obtained in the step 701, so as to obtain a magnetic resonance signal Sw2(L(i))(x(a), y(b), z(c))(t(j)) of a 2-dimensional real-space or a 3-dimensional real-space ((x)a, y(b), z(c)) under non-water-suppressed condition (step 702).

Next, a signal phase value is calculated from the magnetic resonance signal Sw2(L(i)) (x(a), y(b), z(c)) (t(j)) obtained in the step 702, for each real-space point of each element coil L(i) (step 703). All the signals or some of the signals, having data with the number of "J", in a t-axis direction, can be used for calculating the signal phase value, or one data (signal) of which an absolute value of the signal value is comparatively large can be used. In the present embodiment, the phase value $\Phi w(L(i))$ (x(a), y(b), z(c)) (t(N)) of each signal is calculated using the "N"Tth signal Sw2(L(i)) (x(a), y(b), z(c)) (t(N)) from the top, for each element coil L(i). For N, it is preferable to select a point where an absolute value thereof is large, however, it is possible to use any one of the points within a predetermined range (for example from 1 to 20). The phase value $\Phi w(L(i))$ (x(a), y(b), z(c)) (t(N)) of the signal Sw2(L(i)) (x(a), y(b), z(c))(t(N)) can be calculated in accordance with an equation 4.

$$\Phi w(L(i))(x(a),y(b),z(c))(t(N)) = \tan^{-1}\{Im(Sw2(L(i))(x(a),y(b),z(c))(t(N)))/Re(Sw2(L(i))(x(a),y(b),z(c))(t(N)))\} \quad \text{(equation 4)}$$

The obtained signal phase value $\Phi w(L(i))(x(a), y(b), z(c))$ $(t(N))$ of each element coil L (i) is stored in the storage device 11, as a correction value for correcting a signal measured in a main-scan (the water-suppressed measurement), that is, a correction value for the MAC summation. The signal phase value $\Phi w(L(i))$ $(x(a), y(b), z(c))$ $(t(N))$ corresponds to an offset variance component C0 of a signal phase $\Phi(i)$, independent to the data number i as described above.

Next, the water-suppressed measurement as described above is executed so as to obtain a spectral information of the 2-dimensional k-space or the 3-dimensional k-space under a water-suppressed condition for each element coil L(i) (step 704). The obtained k-space spectral information (a magnetic resonance signal) of each element coil L(i), are denoted as Sm1(L(i)) (kx(a), ky(b), kz(c))(t(j)).

Next, an operation for transforming between a k-space component and a real-space component in each axis direction of k-space (for example a inverse Fourier transform) is performed on the k-space magnetic resonance signal Sm1(L(i)) (kx(a), ky(b), kz(c))(t(j)) of each element coils obtained in the step 704, so as to obtain a magnetic resonance signal Sm2(L (i)) (x(a), y(b), z(c))(t(j)) of the 2-dimensional real-space or the 3-dimensional real-space, under the water-suppressed condition (step 705).

Next, a phase correction for matching phases each other among coils is performed by each real-space point of each element coil L(i), on the magnetic resonance signal Sm2(L(i)) (x(a), y(b), z(c)) (t(j)) of the real-space calculated in the step 705 using the signal phase value of the non-water-suppressed signal $\Phi w(L(i))$ (x(a), y(b), z(c)) (t(N)) (the correction value for the MAC summation) calculated in the step 703, so as to obtain a magnetic resonance signal Sm3(L(i)) (x(a), y(b), z(c)) (t(j)) of each real-space point of each element coil L(i) (step 706). This phase correction is performed on all the signals having data with the number of "J in the t-axis direction, and both the real-part and the imaginary-part of each data t(j) are calculated in accordance with following equation 5 and equation 6.

$$Re(Sm3(L(i))(x(a),y(b),z(c))(t(j))) = \cos((-1) \times \Pi \times \Phi w(L(i))(x(a),y(b),z(c))(t(N))/180) \times Re(Sm2(L(i))(x(a),y(b),z(c))(t(j))) - \sin((-1) \times \Pi \times \Phi w(L(i))(x(a),y(b),z(c))(t(N))/180) \times Im(Sm2(L(i))(x(a),y(b),z(c))(t(j)))$$ (Equation 5)

$$Im(Sm3(L(i))(x(a),y(b),z(c))(t(j))) = \sin((-1) \times \Pi \times \Phi w(L(i))(x(a),y(b),z(c))(t(N))/180) \times Re(Sm2(L(i))(x(a),y(b),z(c))(t(j))) + \cos((-1) \times \Pi \times \Phi w(L(i))(x(a),y(b),z(c))(t(N))/180) \times Im(Sm2(L(i))(x(a),y(b),z(c))(t(j)))$$ (Equation 6)

The magnetic resonance signal Sm3(L(i))(x(a), y(b), z(c)) (t(j)) of each real-space point of each element coil calculated in the step 706 is subjected to a complex addition according to following equations of 7 and 8 so as to obtain a value of added magnetic resonance signal Sm4(x(a), y(b), z(c))(t(j)) of each real-space point (step 707).

$$Re(Sm4(x(a), y(b), z(c))(t(j))) = \sum_{i=1}^{I} Re(Sm3(L(i))(x(a), y(b), z(c))(t(j)))$$ (Equation 7)

$$Im(Sm4(x(a), y(b), z(c))(t(j))) = \sum_{i=1}^{I} Im(Sm3(L(i))(x(a), y(b), z(c))(t(j)))$$ (Equation 8)

Further, an operation for transforming between a time component and a frequency component in the time-axis direction (for example an inverse Fourier transform) is performed on the added magnetic resonance signal Sm4(x(a), y(b), z(c)) (t(j)) of each real-space point, calculated in the step 707, so as to obtain a magnetic resonance spectroscopic image Sm5(x(a), y(b), z(c))(f(j)) of the 2-dimensional real-space or the 3-dimensional real-space having information in frequency-axis(f-axis) direction (step 708).

A phase correction (the first order phase component and the 0 order phase component correction) in the spectrum-axis direction is performed on a magnetic resonance spectrum of each pixel of the magnetic resonance spectroscopic image Sm5(x(a), y(b), z(c))(f(j)) of the 2-dimensional real-space or the 3-dimensional real-space, calculated in the step 708.

Figure 7:
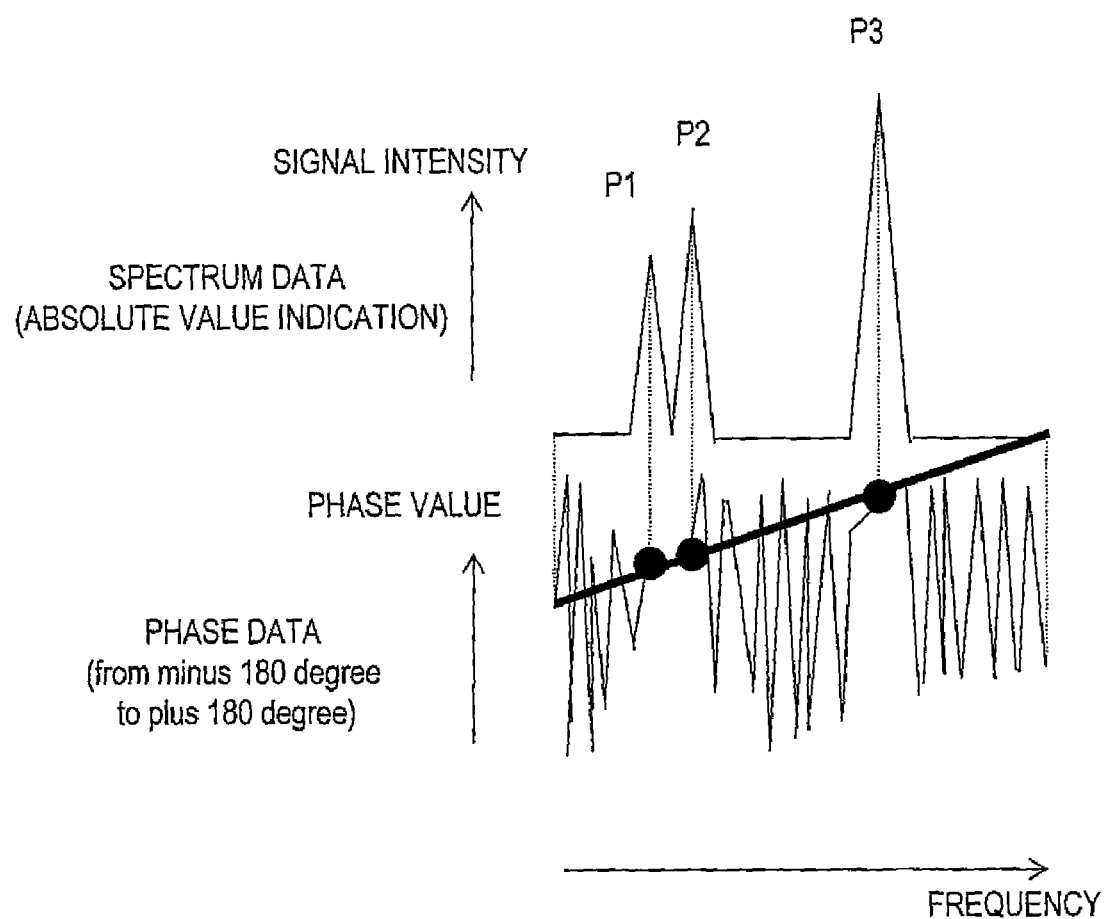
FIG. 7 shows an example of an absolute value and a phase value of a spectrum signal.

Hereinafter, a procedure of the phase correction in the spectrum-axis direction will be described. FIG. 7 shows examples of an absolute value and a phase value of the spectrum signal. In FIG. 7, a lateral axis indicates frequency, vertical axis of the spectrum data indicates an absolute (or square) value of the signal intensity, and vertical axis of phase data indicates the phase value (from minus 180 degree to plus 180 degree). As shown in FIG. 7, a target spectrum signal S (a spectrum data with absolute value indication) for the phase correction has several signal peaks (P1, P2, P3 . . . ) discretely. Areas other than the area where these signal peaks are exist are noise area, and the phase components (phase data) in the noise areas are meaningless data (random values). Therefore, for calculating the phase distortion, it should be started with detecting the signal peaks. The signal peaks are detected by a peak judgment, which judges peaks with a second order differential value and a third order differential value calculated by polynomial conforming method or the like and by setting an adequate threshold value. Then, the phase values at detected signal peaks (black dot points in the FIG. 7) are calculated according to the equation 2. Further, fitting operation to equation 3 is performed on the thus calculated discrete phase values so as to obtain an approximate expression (a black thick line in FIG. 7). For obtaining the approximate expression, a least squares approximation method or the like is applicable. An inclination of the obtained approximate line is corresponded to the C1 above and a vertical-axis intercept of the line is corresponded to the C0 above. The phase correction in the spectrum-axis direction is performed for calculating the phase distortion P(j)=C1×j+C0 of "j"th data of the magnetic resonance spectroscopic image Sm5(x(a), y(b), z(c))(f(j)) using these values so as to obtain a magnetic resonance spectroscopic image Sm6(x(a), y(b), z(c))(f(j)) of the 2-dimensional real-space or the 3-dimensional real-space. Then, a component of the real-part Re(Sm6(x(a), y(b), z(c)) (f(j))) of the magnetic resonance spectroscopic image Sm6(x (a), y(b), z(c)) (f(j)) of the 2-dimensional real-space or the 3-dimensional real-space is extracted (step 709).

As discussed above, in the present embodiment, in case of executing the MRSI measurement using a MAC, the correction value (a correction value for the MAC summation) for matching phases of each pixel of each element coil is calculated using a reference image signal with high SNR obtained in the first measurement without water suppression. Then, correction is performed on the image signal obtained in the main-scan with water suppression pixel-by-pixel for each element coil, using the correction value for the MAC summation. Thereafter, the MAC summation is performed so as to perform the phase correction in the spectrum-axis direction of each pixel on summed signals.

Prior to the MAC summation, a correction for matching only the 0 order component of the phase distortion is performed pixel-by-pixel for each element coil. The phase correction in the spectrum-axis direction, including a correction of the first order component of the phase distortion, is performed for each pixel on a spectrum signal, to which the MAC summation is applied. The 0 order component of the phase distortion is an offset component of the signal phase, independent to the data number. The present embodiment, only the offset component which degrades summation effect largely under the condition where a spatial phase distribution has non-uniformity, is corrected prior to the summation, and the phase correction in the spectrum-axis direction is performed subsequent to the summation.

According to the present embodiment, since the 0 order component of the phase distortion is corrected prior to the MAC summation, it is possible to obtain signals to which the MAC summation is effectively applied under the condition where a spatial phase distribution has non-uniformity. Since the phase correction in the spectrum-axis direction also including the first order component of the phase distortion shall be performed only on one set (one coil) of the magnetic resonance spectroscopic images after the MAC summation is applied, the computational amount for the correction is not proportional to the number of the coils. Therefore, the present embodiment provides shorter processing time than that of the conventional method where all the phase corrections in the spectrum-axis direction are performed for each element coil. Also, since the measurement data with high SNR, obtained without suppressing water, is used as the correction value used for the phase correction for each element coil, the phase correction for each element coil can be done with high accuracy. Therefore, according to the present embodiment, magnetic resonance spectroscopic images to which the MAC summation is applied can be obtained in a short time and with high accuracy.

<Second Embodiment>

Next, a second embodiment of the present invention will be explained. In the present embodiment, using a phase correction value of each element coil obtained by a non-water-suppressed measurement, a phase correction is applied on signals obtained by a water-suppressed measurement executed subsequently for each element coil, in the same manner as the first embodiment. In the present embodiment, however, when signals obtained by the water-suppressed measurement (main-scan) are added (at a time of a MAC summation) weighting coefficients varying with SNR of each element coil is multiplied thereto. The first embodiment is an embodiment where, the weighting coefficients of this embodiment are made to be 1 for all the element coils on all occasions. Hereinafter, regarding the present embodiment, only the configuration different from the first embodiments will be explained.

Figure 8:
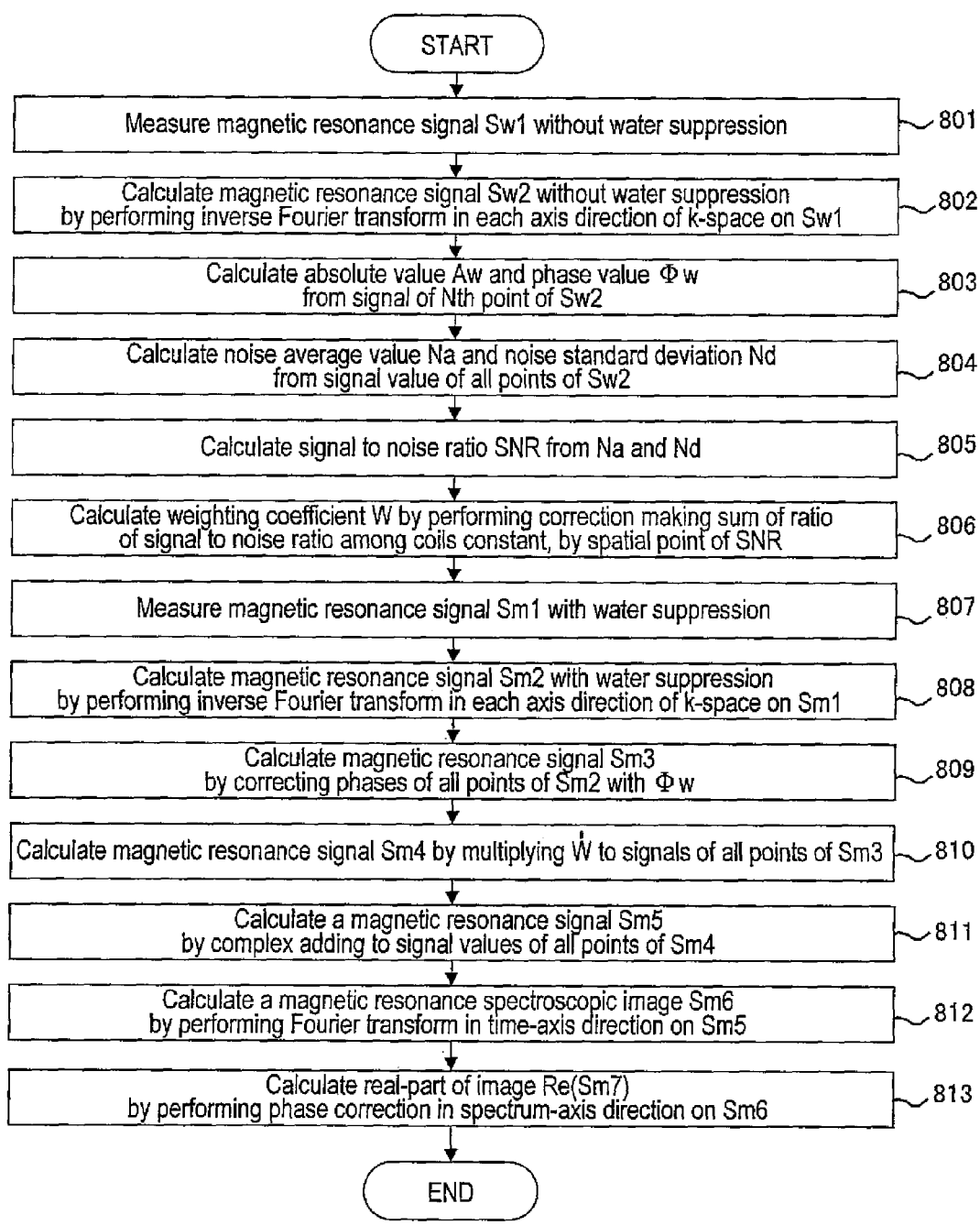
FIG. 8 is a flowchart of the measurement process according to the second embodiment.

The MRSI measurement of the present embodiment is explained. FIG. 8 shows an example of a measurement procedure of the present embodiment. The computer 9 processes each step shown below.

In the present embodiment, first, the non-water-suppressed measurement mentioned above is executed using a receiving coil being made up of multiple element coils L(i) (where, "i" is an integer from 1 to I: i=1, 2, . . . I, representing a coil number) so as to obtain a spectral information (a magnetic resonance signal) denoted as Sw1(L(i))(kx(a), ky(b), kz(c)) (t(j)) (where, "j" is an integer "J" or less representing a data number in time-axis (t-axis) direction), of a 2-dimensional k-space or a 3-dimensional k-space (kx(a), ky(b), kz(c)) (where "a" represents measurement number in a kx-axis direction of an integer "A" or less, "b" represents measurement number in a ky-axis direction of an integer "B" or less, and "c" represents measurement number in a kz-axis direction of an integer "C" or less; in case 2-dimensional measurement, any one of "A", "B", and "C" is 1 and rest of two are integers of 2 or more, and in case 3-dimensional measurement, all of "A", "B", and "C" are integers of 2 or more), under non-water-suppressed condition, by each element coil L(i) (step 801).

Next, an operation for transforming between a k-space component and a real-space component (for example a inverse Fourier transform) is performed on the k-space magnetic resonance signal Sw1(L(i)) (kx(a), ky(b), kz(c)) (t(j)) of each element coil L(i) obtained in the step 801, so as to obtain a magnetic resonance signal Sw2(L(i)) (x(a), y(b), z(c)) (t(j)) of the 2-dimensional real-space or the 3-dimensional real-space ((x)a, y(b), z(c)) under non-water-suppressed condition (step 802).

Next, an absolute value and a phase value of a signal are calculated from the magnetic resonance signal Sw2 (L(i)) (x(a), y(b), z(c))(t(j)) obtained in the step 802, for each of the real-space point of each element coil L(i) (step 803). All or some of the signals, having data with the number of "J" in a t-axis direction, can be used for calculating the absolute value and the phase value, or one data (signal) of which an absolute value of the signal is comparatively large can be used. In the present embodiment, the absolute value Aw(L(i))(x(a), y(b), z(c))(t(N)) and the phase $\Phi$w(L(i))(x(a), y(b), z(c))(t(N)) of each signal are calculated using the "N"th signal Sw2(L(i)) (x(a), y(b), z(c))(t(N)) from the top for each element coil L(i). For N, it is preferable to select a point where an absolute value thereof is large, however, it is possible to use any one of the points within a predetermined range (for example from 1 to 20). The absolute value Aw(L(i))(x(a), y(b), z(c))(t(N)) and the phase value $\Phi$w(L(i))(x(a), y(b), z(c))(t(N)) of the signal Sw2(L(i)) (x(a), y(b), z(c))(t(N)) can be calculated in accordance with following equations 9 and 10.

$$Aw(L(i))(x(a),y(b),z(c))(t(N))=\sqrt{\{(Re(Sw2(L(i))(x(a),y(b),z(c))(t(N)))^2+(Im(Sw2(L(i))(x(a),y(b),z(c))(t(N))^2)\}} \quad \text{(Equation 9)}$$

$$\Phi w(L(i))(x(a),y(b),z(c))(t(N))=\tan^{-1}\{Im(Sw2L(i))(x(a),y(b),z(c))(t(N)))/Re(Sw2(L(i))(x(a),y(b),z(c))(t(N)))\} \quad \text{(Equation 10)}$$

The obtained absolute value Aw(L(i))(x(a),y(b),z(c))(t(N)) and phase value $\Phi$w(L(i))(x(a), y(b), z(c))(t(N)) of "N"th signal of each element coil L (i) are stored in the storage device 11, as a correction value for correcting the signal measured in a main-scan (the water-suppressed measurement).

A noise average and a noise standard deviation are calculated on the magnetic resonance signal Sw2(L(i))(x(a), y(b), z(c)) (t(j)) of the real-space calculated in the step 802, for each real-space point of each element coil L(i). It is preferable the noise average and the noise standard deviation are calculated using the signal where the absolute value Aw(L(i)) (x(a),y(b), z(c))(t(N)) thereof is small. In the present embodiment, the noise average Na(L(i))(x(a), y(b), z(c)) and the noise standard deviation Nd(L(i))(x(a), y(b), z(c)) are calculated in accordance with following equation 11 and equation 12, using the absolute values of the last M points, from Aw(L(i))(x(a), y(b), z(c)) (t(J−M+1)) to Aw(L(i))(x(a), y(b), z(c))(t(J)) among the data that make up the signal Sw2(L(i))(x(a), y(b), z(c))(t(j)) (step 804).

$$Na(L(i))(x(a), y(b), z(c)) = \frac{\sum_{k=1}^{M} Aw(L(i))(x(a), y(b), z(c))(t(n - M + k))}{M} \quad \text{(Equation 11)}$$

$$Nd(L(i))(x(a), y(b), z(c)) = \frac{\sqrt{\sum_{k=1}^{M} \{Aw(L(i))(x(a), y(b), z(c))(t, (n - M + k)) - Na(L(i))(x(a), y(b), z(c))\}^2}}{(M)} \quad \text{(Equation 12)}$$

As described above, for M, it is preferable to select a point of which the absolute value $Aw(L(i))(x(a),y(b),z(c))(t(N))$ of $Sw2(L(i))(x(a), y(b), z(c))(t(M))$ is small, however, it may be possible to use a value of a fixed point selected between 16th and 32nd point from the end of the data, for example.

Further, a signal to noise ratio $SNR(L(i))(x(a), y(b), z(c))$ of each element coil $L(i)$ is calculated in accordance with a following equation 13, using the absolute value $Aw(L(i))(x(a), y(b), z(c))(t(N))$ obtained in the step 803, the noise average $Na(L(i))(x(a), y(b), z(c))$, and the noise standard deviation $Nd(L(i))(x(a), y(b), z(c))$ obtained in the step 804 (step 805).

$$SNR(L(i))(x(a),y(b),z(c))=(Aw(L(i))(x(a),y(b),z(c))(N)-Na(L(i))(x(a),y(b),z(c)))/Nd(L(i))(x(a),y(b),z(c)) \quad \text{(Equation 13)}$$

Then, a coefficient (weighting coefficient $W(L(i))(x(a),y(b),z(c))$), which makes a sum of ratio $R(L(i))(x(a),y(b),z(c))$ constant, is calculated for each spatial point, for each element coil $L(i)$, where $R(L(i))(x(a),y(b),z(c))$ is a ratio of the signal to noise ratio among coils, detected at each element coil, of a spatial point (a ratio with respect to the maximum signal to noise ratio) (step 806).

For example, equations are shown, where the signal to noise ratio on the spatial point $(x(0),y(0),z(0))$, detected by four element coils $L(1)$, $L(2)$, $L(3)$, and $L(4)$ respectively, is expressed as following equation 14, equation 15, equation 16 and equation 17.

$$SNR(L(1))(x(0),y(0),z(0))=e \quad \text{(Equation 14)}$$

$$SNR(L(2))(x(0),y(0),z(0))=f \quad \text{(Equation 15)}$$

$$SNR(L(3))(x(0),y(0),z(0))=g \quad \text{(Equation 16)}$$

$$SNR(L(4))(x(0),y(0),z(0))=h \quad \text{(Equation 17)}$$

In this case, the ratio $R(L(i))(x(a),y(b),z(c))$ of the signal to noise ratio among coils, is expressed as following equation 18, equation 19, equation 20 and equation 21.

$$R(L(1))R(L(0))(x(0),y(0),z(0))=e/\max(e,f,g,h)=E \quad \text{(Equation 18)}$$

$$R(L(2))R(L(1))(x(0),y(0),z(0))=f/\max(e,f,g,h)=F \quad \text{(Equation 19)}$$

$$R(L(3))R(L(2))(x(0),y(0),z(0))=g/\max(e,f,g,h)=G \quad \text{(Equation 20)}$$

$$R(L(4))R(L(3))(x(0),y(0),z(0))=h/\max(e,f,g,h)=H \quad \text{(Equation 21)}$$

Here, $\max(e, f, g, h)$ is defined as a function returning the maximum value among "e", "f", "g" and "h".

The coefficient $W(L(i))(x(a),y(b),z(c))$, which makes the sum of the ratio $R(L(i))(x(a),y(b),z(c))$ of the signal to noise ratio among coils, of all the element coils $L(i)$, at the spatial point $(x(0),y(0),z(0))$ constant value P, is expressed as following equation 22, equation 23, equation 24 and equation 25 for 4 element coils of $L(1)$, $L(2)$, $L(3)$, and $L(4)$, respectively.

$$W(L(1))(x(0),y(0),z(0))=E \times P/(E+F+G+H) \quad \text{(Equation 22)}$$

$$W(L(2))(x(0),y(0),z(0))=F \times P/(E+F+G+H) \quad \text{(Equation 23)}$$

$$W(L(3))(x(0),y(0),z(0))=G \times P/(E+F+G+H) \quad \text{(Equation 24)}$$

$$W(L(4))(x(0),y(0),z(0))=H \times P/(E+F+G+H) \quad \text{(Equation 25)}$$

The thus calculated coefficient $W(L(i))(x(a),y(b),z(c))$ is stored in the storage device 11 as weighting coefficients using for adding operation (MAC summation) described below. For the value P, any value can be set, since a ratio of pixel density value between pixels in the magnetic resonance spectroscopic image may be kept constant, as long as an identical value is set for P throughout the process for processing a set of magnetic resonance spectroscopic image signals. For example, the number of the element coils (four in the above calculation example) can be set constant.

Next, the water-suppressed measurement as mentioned above is executed so as to obtain spectral information (a magnetic resonance signal) $Sm1(L(i))(kx(a), ky(b), kz(c))(t(j))$ of the 2-dimensional k-space or the 3-dimensional k-space for each element coil, under water suppression (step 807).

Next, an operation for transforming between a k-space component and a real-space component (for example, the inverse Fourier transform) in each axis direction of k-space is performed on a magnetic resonance signal $Sm1(L(i))(kx(a), ky(b) kz(c))(t(j))$ of the k-space obtained at each element coil in the step 807, so as to calculate a magnetic resonance signal $Sm2(L(i))(x(a), y(b), z(c))(t(j))$ of a 2-dimentional real-space or a 3-dimentional real-space $(x(a), y(b), z(c))$ under water-suppressed condition (step 808).

Next, a phase correction for matching phases each other among coils is performed on the magnetic resonance signal $Sm2(L(i))(x(a), y(b), z(c))(t(j))$ of the real-space calculated in the step 808, using the phase value $\Phi w(L(i))(x(a), y(b), z(c))(t(N))$ of the signal acquired without water suppression calculated in the step 803, for each real-space point in each element coil, so as to obtain a magnetic resonance signal $Sm3(L(i))(x(a), y(b), z(c))(t(j))$ of each real-space of each element coil (step 809). Here, all the signals having data with the number of "J" in the t-axis direction, are subjected to the phase correction, and a real-part and imaginary-part of each data $t(j)$ are calculated in accordance with following equation 26 and equation 27.

$$Re(Sm3(L(i))(x(a),y(b),z(c))(t(j)))=\cos((-1) \times \Pi \times \Phi w(L(i))(x(a),y(b),z(c))(t(N))/180) \times Re(Sm2(L(i))(x(a),y(b),z(c))(t(j)))-\sin((-1) \times \Pi \times \Phi w(L(i))(x(a),y(b),z(c))(t(N))/180) \times Im(Sm2(L(i))(x(a),y(b),z(c))(t(j))) \quad \text{(Equation 26)}$$

$$Im(Sm3(L(i))(x(a),y(b),z(c))(t(j)))=\sin((-1) \times \Pi \times \Phi w(L(i))(x(a),y(b),z(c))(t(N))/180) \times Re(Sm2(L(i))(x(a),y(b),z(c))(t(j)))+\cos((-1) \times \Pi \times \Phi w(L(i))(x(a),y(b),z(c))(t(N))/180) \times Im(Sm2(L(i))(x(a),y(b),z(c))(t(j))) \quad \text{(Equation 27)}$$

Then, the weighting coefficient obtaiend in the step 806 is multiplied to the magnetic resonance signal $Sm3(L(i))(x(a), y(b), z(c))(t(j))$ of each point of real-space in each element coil, obtained in the step 809 so as to obtain Sm4(L(i))(x(a), y(b), z(c))(t(j)) (step 810). In the process, the real-part and the imaginary-part of each data t(j) is calculated in accordance with following equation 28 and equation 29.

$$Re(Sm4(L(i))(x(a),y(b),z(c))(t(j)))=Re(Sm3(L(i))(x(a),y(b),z(c))(t(j)))\times W(L(i))(x(a),y(b),z(c))(t(N)) \quad \text{(Equation 28)}$$

$$Im(Sm4(L(i))(x(a),y(b),z(c))(t(j)))=Re(Sm3(L(i))(x(a),y(b),z(c))(t(j)))\times W(L(i))(x(a),y(b),z(c))(t(N)) \quad \text{(Equation 29)}$$

Then, the magnetic resonance signal Sm4(L(i))(x(a), y(b), z(c))(t(j)) of each real-space point of each element coil calculated in the step 810 is subjected to a complex addition in accordance with the following equation 30 and equation 31, so as to obtain a magnetic resonance signal value Sm5(x(a), y(b) z(c))(t(j)) of each real-space point (step 811).

$$Re(Sm5(x(a), y(b), z(c))(t(j))) = \sum_{i=1}^{I} Re(Sm4(L(i))(x(a), y(b), z(c))(t(j))) \quad \text{(Equation 30)}$$

$$Im(Sm5(x(a), y(b), z(c))(t(j))) = \sum_{i=1}^{I} Im(Sm4(L(i))(x(a), y(b), z(c))(t(j))) \quad \text{(Equation 31)}$$

Further, an operation for transforming between a time component and a frequency component in a time-axis direction (for example a Fourier transform) is performed on the added magnetic resonance signal value Sm5(x(a), y(b), z(c))(t(j)) of each real-space point calculated in the step 811 so as to obtain a magnetic resonance spectroscopic image Sm6(x(a), y(b), z(c))(f(j)) of the 2-dimentional real-space or the 3-dimentional real-space, having an information in a frequency-axis direction(step 812).

Then, a phase correction in a spectrum-axis direction (a phase correction for both of a first order phase component and a 0 order phase component) is performed on a magnetic resonance spectrum of each pixel of the magnetic resonance spectroscopic image Sm6(x(a), y(b), z(c))(f(j)) of the 2-dimentional real-space or the 3-dimentional real-space obtained in the step 812 in the same manner as in the first embodiment, so as to obtain a real part component Re(Sm7(x(a), y(b), z(c))(f(j))) of the magnetic resonance spectroscopic image of the 2-dimentional real-space or the 3-dimentional real-space(step 813).

As described above, conventionally, an equivalent summation with the weighting coefficient of 1 is performed when adding signals obtained at each coil. According to the present embodiment, a SNR of each pixel of each coil is calculated from image signals acquired by a reference measurement without suppressing water, then, the summation is performed to signals acquired by the main-scan with water suppression, after the coefficient calculated from the SNR of each pixel of each coil is multiplied thereto.

According to the present embodiment, in case of performing the MRSI measurement using the MAC, the phase correction value for matching the phase of each pixel of each element coil and the weighting value for the MAC summation are calculated using the reference image signal having a high SNR obtained in the first measurement without water suppression, and then, the phase correction is performed on the image signals acquired in the main-scan with water suppression, using the calculated phase correction value prior to applying the MAC summation, where the weight coefficient is calculated at the MAC summation. Specifically, prior to the MAC summation, the correction for matching only 0 order component of the phase distortion is performed and the correction with regard to the first order component of the phase distortion, is performed on the spectrum signal after applying the MAC summation.

According to the present embodiment, signals, to which the MAC summation is effectively applied, can be obtained even if a spatial phase distribution has non-uniformity, the same as in the first embodiment. Also, since the phase correction in the spectrum-axis direction shall be performed only on one set (one coil) of the magnetic resonance spectroscopic image after applying the MAC summation, the computational amount for the correction is not proportional to the number of the coils. Therefore, the present embodiment provides shorter processing time than that of the conventional method where all the phase corrections in the spectrum-axis direction are performed for each element coil. Also, since the measurement data with high SNR, obtained without water suppression, is used as the correction value used for the phase correction for each element coil, the phase correction for each element coil can be done with high accuracy. Further, the weighting coefficient prevents a degradation of the MAC summation signals caused by a variation even the SNR of each element coil that makes up the receiving coil has the variation. Therefore, according to the present embodiment, magnetic resonance spectroscopic images to which the MAC summation is applied can be obtained in short time and with high accuracy.

Each embodiment of a magnetic resonance imaging apparatus employed the present invention has been explained above. The present invention is not limited to above-mentioned embodiments and various changes and modifications can be applicable. For example, the arrangement of element coils that make up the receiving coil can be flat. A shape of each element coil is not limited to a plane-shaped but may have a curved surface depending on an inspection part. In above embodiments, the non-water-suppressed measurement is executed as the first measurement, and water-suppressed measurement is executed as the second measurement, however, the order of measurements can be replaceable. So as to say, the water-suppressed measurement can be executed as the first measurement, and the non-water-suppressed measurement can be executed as the second measurement. In the above embodiments, a case is exemplified where the MRSI measurement is assumed to be executed with the pulse sequence of region selective spin-echo type. However, the pulse sequence used for the measurement is not limited to this. All the pulse sequences so long as the MRSI measurement can be executed may bring the same effect. For example, measurement sequences without region selection, called 3D-CSI and 4D-CSI, or a fast measurement sequence with a fast switching gradient magnetic field, called EPSI, may bring the same effect.

In each embodiment described above, the reference measurement for calculating the correction value is performed to obtain spectral information of the 2-dimention k-space or the 3-dimention k-space under the non-water-suppressed condition. However, executing the nun-water-suppressed measurement using the pulse sequence shown in FIG. 4 consumes a measurement time depending on the measurement condition; the extension of the measurement time can be reduced by following method.

For example, provided that the application intensity of the gradient magnetic field Gp1, Gp2, and Gp3 varies 16 steps for Gp1, 16 steps for Gp2, and 1 step for Gp3, respectively, and the measurements is to be repeated 256 (=16×16×1) times in 2 seconds repetition time, a time required for the reference measurement takes 512 seconds (8 minutes and 32 seconds).

Therefore, the total measurement timer including the non-water-suppressed measurement time and the water-suppressed measurement time becomes 1024 seconds (17 minutes and 4 seconds), twice as long as the reference measurement, and is rather too long for clinical application.

Figure 9:
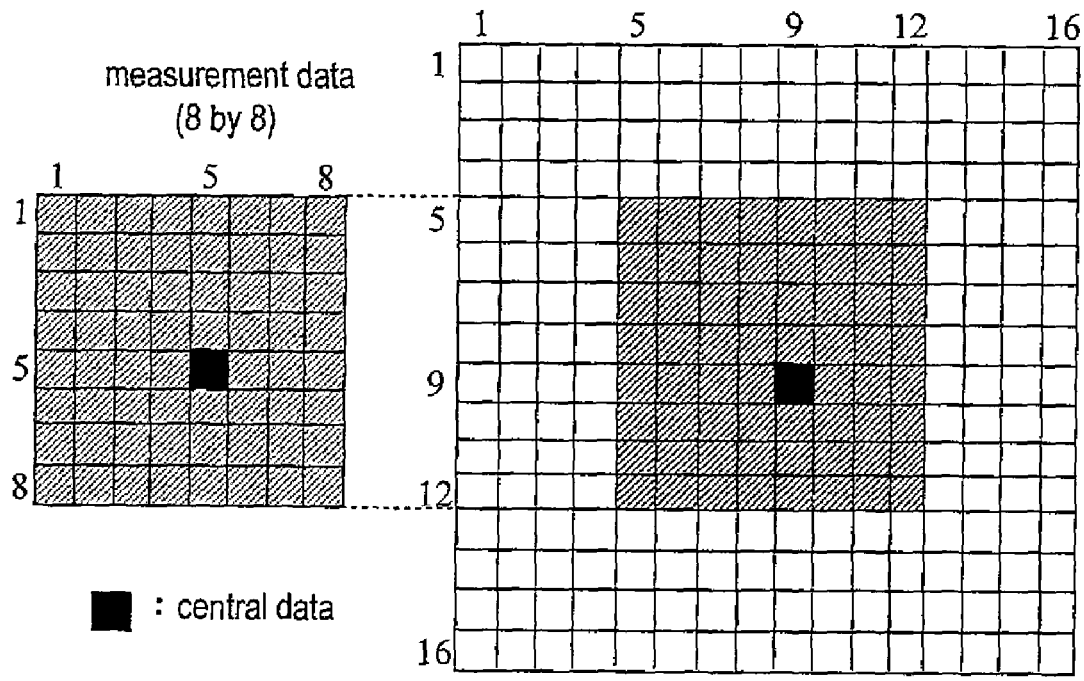
FIG. 9 illustrates a concept of the zero-filling.

To reduce the time required for the reference measurement, the number of repeating times is reduced. Specifically, only the number of steps of the gradient magnetic field for phase encode is reduced without changing the step width thereof. For example, only steps of the application intensity of each of the phase encoding gradient magnetic fields Gp1, Gp2, and Gp3 in the above mentioned example, are reduced to one-half in number, such as 8 steps for Gp1, 16 steps for Gp2, and 1 step for Gp3, without changing the step width thereof so that the measurement time can be reduced to 128 seconds (2 minutes and 8 seconds) i.e., a quarter. When using the measurement data obtained through the non-water-suppressed measurement with reduced phase encoding steps as a reference image, just as it is, a spatial resolution of the non-water-suppressed measurement image are different from that of the water-suppressed measurement image so that the phase correction mentioned above can not be applied straightforwardly. Therefore, the two spatial resolutions equate to each other using the following technique called zero-filling Hereinafter, a specific procedure of zero-filling is roughly explained with reference to the FIG. 9. When the number of phase encoding steps in the water-suppressed measurement is 16×16×1, if the number of the phase encoding steps in the non-water-suppressed measurement is reduced to 8×8×1 without changing step width thereof and the time required for the reference measurement is reduced to a quarter (one-half× one-half), the pixel size of the image obtained through the reconstruction processing becomes 4 times (2×2×1). As shown in FIG. 9, the data of 8×8×1 (time series signal of 8×8×1) obtained through the reference measurement, are allocated in the center part of the matrix (reconstruction matrix) of 16×16×1, and zero-data is filled around the perimeter of the matrix where data are missing. An inverse Fourier transform is, then, performed in a phase encode-axis direction to equate the pixel size with the size where the number of phase encoding steps is 16×16×1.

In the zero-filling operation, the process, such as, detecting the true point of zero-encoded of the measurement data (the point having the strongest intensity among a spatial distribution) so as to center it, multiplying the Hamming function or the like on the spatial distribution to the measurement data so as to correct the data in the center of the measurement having the maximum signal intensity, can be carried out when allocating the measured data on the reconstruction matrix.

There is a way to reduce the repetition time as the other way to reduce the time required for the reference measurement. For example, when the repetition time of 2 seconds shown in the above example is reduced to one-half, the measurement time can be one-half, 256 seconds (4 minutes 16 seconds). However, if the repetition time is simply to be reduced, the relaxation time affects and changes an initial state of the nuclear magnetization so as to raise the possibility of failing to have proper phase information. In such a case, the flip angle of the radiofrequency magnetic field for excitation used in the non-water-suppressed measurement can be set smaller than that of in the water-suppressed measurement so as to reduce the relaxation time effect, under the condition of making the repetition time shorter.

There may be cases where the repetition time cannot simply make shorter since the echo time ("TE" in the FIG. 4) or the signal detection time (a measurement time of the signal Sig 1 in the FIG. 4) is long. In such case, the echo time (TE) using in the non-water-suppressed measurement set to be shorter than that of using in the water-suppressed measurement. In other words, the starting time for detection of the magnetic resonance signal emitted from the subject in the non-water-suppressed measurement is set ahead of that in the water-suppressed measurement. Thus, the repetition time can be reduced.

Also, a signal detection time of the non-water-suppressed measurement can be set shorter than that of the water-suppressed measurement so as to reduce the repetition time.

If the signal detection time of the non-water-suppressed measurement is set to be extremely short, an eddy current correction, where the time variance among the signal detection time in the non-water-suppressed measurement is used as a reference, can not be carried out. In such a case, a correction equivalent to the eddy current correction is performed with adding the post-process, such as aligning the peak positions of metabolite (for example, N-acetylaspartic acid) having the highest signal intensity in the water-suppressed measurement image.

Also, the present invention can be applied to a measurement called parallel imaging (parallel MRSI measurement), where an "aliased image" caused by reducing the applied step width of the intensity of the phase encoding gradient magnetic field is corrected using a sensitivity map of each receiving coil so as to reduce the scan time, in the MRSI measurement using the magnetic resonance imaging apparatus provided with the multi-array coil (MAC). The magnetic resonance spectroscopic image of high SNR obtained through the reference measurement without water suppression may be used as the sensitivity map.

When the MRSI measurement according to the pulse sequence shown in above FIG. 4 is performed with two receiving coils, if the step width of application intensity of phase encoding gradient magnetic field Gp1 in the x-axis direction makes double and the number of steps thereof reduces to one-half, the measurement time can be reduced to one-half at the same time, and a field of view in the x-axis direction becomes also in one-half. The image with a field of view of one-half has an aliasing of the subject. Therefore, in the parallel MRSI imaging, the image of full field of view is reconstructed with separating the aliasing by solving simultaneous equations using sensitivity difference between the two coils (refer to, J. B. Ra, C. Y. Rim: Fast Imaging Using Subencoding Data Sets from Multiple Detectors, Magnetic Resonance in Medicine, vol. 30, pp. 142-145 (1993)). Since the magnetic resonance spectroscopic image of high SNR obtained through the reference measurement without water suppression is used as the sensitivity map image, accuracy of aliasing separation is enhanced.

EXAMPLE

Examples of the first embodiment and the second embodiment are shown below. Here, the pulse sequences shown in FIG. 5 and FIG. 4 was executed as the MRSI measurement, using the magnetic resonance imaging apparatus of the type shown in FIG. 1A equipped with a multi-array coil (cylindrical coil) shown in the FIG. 3, where an intensity of the static magnetic field is 1.5 tesla. A target nuclide was a proton, and a target subject for measurement was a phantom fulfilled with a water solution of N-acetylealanine.

Figure 10A:
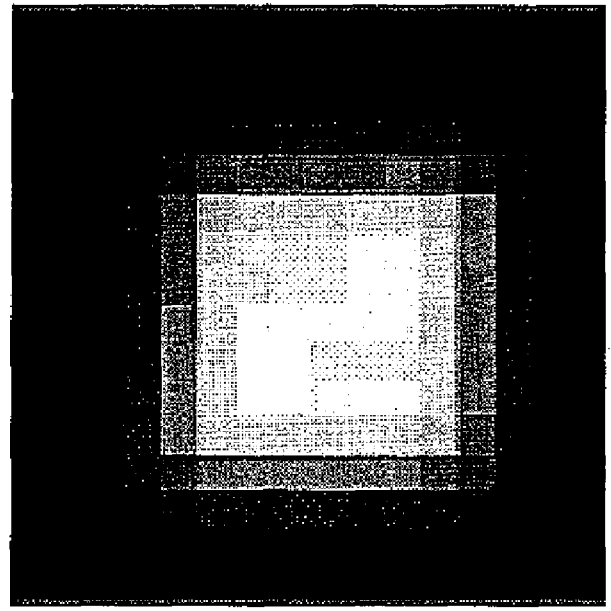
FIG. 10A shows a specific example of the first embodiment.
Figure 10B:
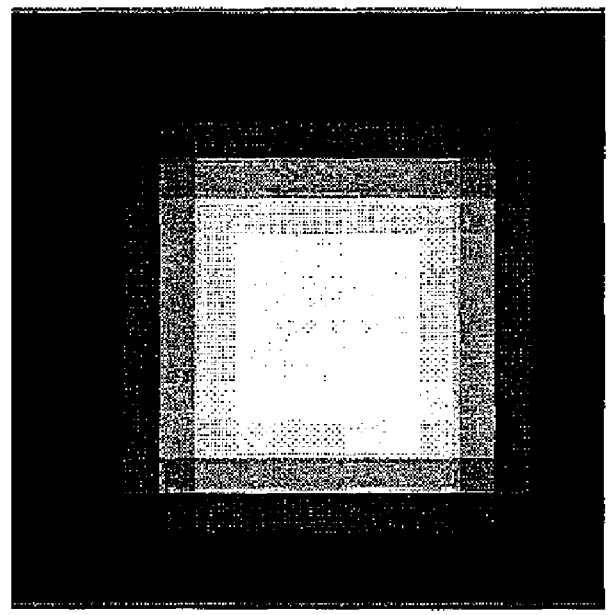
FIG. 10B shows a specific example of the second embodiment.

FIG. 10 shows a resultant spectroscopic image after the MAC summation was applied. FIG. 10A shows a result where the MAC summation was applied according to the procedure shown in FIG. 6, and FIG. 10B shows a result where the MAC summation was applied according to the procedure shown in FIG. 8. In both images, inside a selective excitation region is depicted as a uniform signal area in general, and this means that summed images having a uniform intensity distribution reflecting essentially uniform density distribution of a water solution in the phantom are obtained. In the image shown in FIG. 10A, lower-left part in the selective excitation region is drawn as an area with relatively high intensity. This is assumed to come from a variation in receiving sensitivity among receiving coils. The image shown in FIG. 10B shows that the non-uniformity is also resolved.

Denotation of the Reference Numerals

1: subject, 2: static magnetic field coil, 3: gradient magnetic field coil, 4: shim coil, 5: radiofrequency coil for transmitting, 6: radiofrequency coil for receiving, 7: transmitter, 8: receiver, 9: computer, 10: display, 11: storage device, 12: power supply for gradient magnetic field, 13: power supply for shim, 14: sequence controller, 15: input device.

What is claimed is:

1. A magnetic resonance imaging apparatus comprising:
a magnetic field generating means for generating a static magnetic field, a radiofrequency magnetic field and a gradient magnetic field, respectively;
a detecting means for detecting a magnetic resonance signal generated from a subject placed in the static magnetic field;
a measurement control means for controlling the magnetic field generating means and the detecting means; and
a computing means for reconstructing a magnetic resonance spectroscopic image using a nuclear magnetic resonance signal, so as to display the magnetic resonance spectroscopic image, where,
the detecting means includes a receiving coil being made up of multiple element coils; wherein,
the measurement control means includes,
a first measurement sequence means for performing a first measurement sequence for measuring a nuclear magnetic resonance spectrum without suppressing a nuclear magnetic resonance signal from water, and
a second measurement sequence means for performing a second measurement sequence for measuring a nuclear magnetic resonance spectrum with suppressing a nuclear magnetic resonance signal from water, and,
the computing means calculates a signal phase value of each pixel using the nuclear magnetic resonance signal of each pixel measured at each of the multiple element coils in the first measurement sequence means, and performs a phase correction for each nuclear magnetic resonance signal of each pixel measured at each of the multiple element coils in the second measurement sequence means using the signal phase value above-mentioned, in summing images reconstructed for each of the multiple element coils.

2. The magnetic resonance imaging apparatus according to the claim 1, wherein,
the computing means calculates a weighting coefficient according to a signal to noise ratio of each of the multiple element coils, of each pixel measured by each of the multiple element coils, using the magnetic resonance signal of each pixel measured for each of the element coils in the first measurement sequence means, and multiplies the weighting coefficient to the signal of each pixel measured by each of the multiple element coils when summing images reconstructed for each element coil.

3. The magnetic resonance imaging apparatus according to the claim 1, wherein,
the computing means performs a phase correction in a spectrum-axis direction on the summed nuclear magnetic resonance spectrum of each pixel calculated from the nuclear magnetic resonance signal of each pixel obtained by the summation after the phase correction.

4. The magnetic resonance imaging apparatus according to claim 1, wherein,
the measurement control means sets a number of steps of a magnetic gradient field application, for a phase encoding, in at least one axis direction among the gradient magnetic fields which are generated by the magnetic field generating means in the first measurement sequence, to be less than that of the magnetic gradient fields in at least one axis direction generated by the magnetic field generating means in the second measurement sequence.

5. The magnetic resonance imaging apparatus according to claim 1, wherein,
the measurement control means sets a repetition time for repeating a nuclear magnetic resonance signal measurement used in the first measurement sequence to be shorter than the repetition time used in the second measurement sequence.

6. The magnetic resonance imaging apparatus according to the claim 5, wherein,
the measurement control means sets a flip angle of a radiofrequency magnetic field for excitation generated by the magnetic field generating means used in the first measurement sequence to be smaller than the flip angle used in the second measurement sequence.

7. The magnetic resonance imaging apparatus according to claim 1, wherein,
the measurement control means sets a detection starting time where the detecting means starts for detecting a magnetic resonance signal generated from the subject in the first measurement sequence to be earlier than the detection starting time in the second measurement sequence.

8. The magnetic resonance imaging apparatus according to claim 1, wherein,
the measurement control means sets a detecting time where the detecting means detects a magnetic resonance signal from the subject in the first measurement sequence to be shorter than the detecting time in the second measurement sequence.

9. A method for calculating a magnetic resonance spectroscopic image from a magnetic resonance signal obtained by irradiating a radiofrequency magnetic field to a subject placed in a static magnetic field at least once, applying a gradient magnetic field to the subject at least once after the irradiation of the radiofrequency magnetic field, and detecting the magnetic resonance signal generated from the subject at a receiving coil after the application of the gradient magnetic field, wherein,
the receiving coil is a multi-array coil (MAC) being made up of multiple element coils L(i) (here, i denotes an integer from 1 to I: i=1, 2, . . . I, representing a coil number), and
the method comprising,
a first measuring step for measuring a spectral information of a 2-dimensional k-space or a 3-dimensional k-space (kx(a), ky(b), kz(c)) (where "a" represents measurement number in a kx-axis direction of an integer "A" or less, "b" represents measurement number in a ky-axis direction of an integer "B" or less, and "c" represents measurement number in a kz-axis direction of an integer "C" or less; wherein in a case of 2-dimensional measurement, any one of "A", "B", and "C" is 1 and a remaining two of "A", "B", and "C" are integers of 2 or more, and in a case of 3-dimensional measurement, all of "A", "B", and "C" are integers of 2 or more), under a non-water-suppressed condition, a first k-space and real-space transform step for performing a transform between a k-space component and a real-space component in each k-space axis (kx, ky, kz) direction on a magnetic resonance signal Sw1(L(i))(kx(a), ky(b), kz(c))(t(j)) (where, "j" is an integer "J" or less representing a data number in a time-axis (t-axis) direction) acquired at each element coil in the first measurement step, so as to calculate a magnetic resonance signal in a 2-dimensional real-space or a 3-dimensional real-space (x(a), y(b), z(c)), a phase value calculating step for calculating a phase value Φw(L(i))(x(a), y(b), z(c))(t(N)) of a "N"th signal Sw2(L(i))(x(a), y(b), z(c))(t(N)) from the top for each real-space point of each element coil, as for the magnetic resonance signal Sw2(L(i))(x(a), y(b), z(c))(t(j)) of the real-space calculated in the first k-space and real-space transform step, so as to obtain a correction value from the calculation result, a second measurement step for measuring a spectral information of the 2-dimensional k-space or the 3-dimensional k-space (kx(a), ky(b), kz(c)), under a water-suppressed condition, a second k-space and real-space transform step for performing a transform between a k-space component and a real-space component, in each k-space axis direction, on a k-space magnetic resonance signal Sm1(L(i))(kx(a), ky(b), kz(c))(t(j)) acquired at the each element coil in the second measurement step, so as to calculate a magnetic resonance signal in the 2-dimensional real-space or the 3-dimensional real-space (x(a), y(b), z(c)), a phase value correction step for performing a phase correction, where the phase values Φm(L(i))(x(a), y(b), z(c))(t(j)) of all the points are corrected point-by-point of each real-space point of each element coil, using the correction value calculated in the phase value calculating step, on the magnetic resonance signal Sm2(L(i))(x(a), y(b), z(c))(t(j)) acquired in the second k-space and real-space transform step, so as to calculate a phase corrected magnetic resonance signal Sm3(L(i))(x(a), y(b), z(c))(t(j)), a MAC summation step for a complex addition of the magnetic resonance signal Sm3(L(i))(x(a), y(b), z(c))(t(j)) of each real-space point of each element coil calculated in the phase value correction step, for each real-space point, so as to make an added signal value Sm4(x(a), y(b), z(c))(t(j)) as a magnetic resonance signal value applied the MAC summation, where multiple images obtained by the MAC are added to each other, a time and frequency transform step for performing a transform between a time component and a frequency component in a time-axis direction on a magnetic resonance signal value Sm4(x(a), y(b), z(c))(t(j)), which is a signal value of each real-space point of the magnetic resonance signal value after the MAC summation, calculated in the MAC summation step, so as to calculate a magnetic resonance spectroscopic image Sm5(x(a), y(b), z(c))(f(j)) of the 2-dimensional real-space or the 3-dimensional real-space having information in a frequency axis (f-axis) direction.

10. The method for calculating a magnetic resonance spectroscopic image according to claim 9, further comprising, a second phase value correction step for performing a phase correction in a spectrum-axis direction on the magnetic resonance spectroscopic image Sm5(x(a), y(b), z(c))(f(j)) of the 2-dimensional real-space or the 3-dimensional real-space having information in the frequency axis (f-axis) direction calculated in the time and a frequency transform step so as to calculate a magnetic resonance spectroscopic image Sm6(x(a), y(b), z(c))(f(j)) of the 2-dimensional real-space or the 3-dimensional real-space.

11. The method for calculating a magnetic resonance spectroscopic image according to claim 9, further comprising, a sensitivity calculating step for calculating a sensitivity distribution of each element coil using the magnetic resonance signal acquired in each element coil in the first measurement step, and further comprising instead of the MAC summation step, a summation step for performing an operation for correcting an aliasing in an image, using the magnetic resonance signal at each real-space point in each element coil calculated in the phase value correction step and the sensitivity distribution for each element coil calculated in the sensitivity calculating step so as to summed multiple images obtained at each element coil.

12. A method for calculating a magnetic resonance spectroscopic image from a magnetic resonance signal obtained by irradiating a radiofrequency magnetic field to a subject placed in a static magnetic field at least once, applying a gradient magnetic field to the subject at least once after the irradiation of the radiofrequency magnetic field, and detecting the magnetic resonance signal generated from the subject at a receiving coil after the application of the gradient magnetic field, wherein, the receiving coil is a multi-array coil (MAC) being made up of multiple element coils L(i) (here, i denotes an integer from 1 to I: i=1, 2, . . . I, representing a coil number), and the method comprising, a first measuring step for measuring a spectral information of a 2-dimensional k-space or a 3-dimensional k-space (kx(a), ky(b), kz(c)) (where "a" represents a measurement number in a kx-axis direction of an integer "A" or less, "b" represents a measurement number in a ky-axis direction of an integer "B" or less, and "c" represents a measurement number in a kz-axis direction of an integer "C" or less;

wherein in a case of 2-dimensional measurement, any one of "A", "B", and "C" is 1 and a remainder of "A", "B", and "C" are integers of 2 or more, and in a case of 3-dimensional measurement, all of "A", "B", and "C" are integers of 2 or more), under a non-water-suppressed condition, a first k-space and real-space transform step for performing a transform between a k-space component and a real-space component in each k-space axis (kx, ky, kz) direction on a magnetic resonance signal Sw1(L(i))(kx(a), ky(b), kz(c))(t(j)) (where, "j" is an integer "J" or less representing a data number in time-axis (t-axis) direction) acquired at each element coil in the first measurement step, so as to calculate a magnetic resonance signal in a 2-dimensional real-space or a 3-dimensional real-space (x(a), y(b), z(c)), an absolute value and phase value calculating step for calculating an absolute value Aw(L(i))(x(a), y(b), z(c))(t(N)) and a phase value Φw(L(i))(x(a), y(b), z(c))(t(N)) of a "N"th signal Sw2(L(i))(x(a), y(b), z(c))(t(N)) from the top for each real-space point of each element coil, as for the magnetic resonance signal $Sw2(L(i))(x(a), y(b), z(c))(t(j))$ of the real-space calculated at the first k-space and real-space transform step, so as to obtain a correction absolute value and a correction phase value from the calculation result, respectively, a noise calculating step for calculating a noise average value $Na(L(i))(x(a), y(b), z(c))$ and a noise standard deviation $Nd(L(i))(x(a), y(b), z(c))$ for each real-space point of each element coil from absolute value signals of predetermined number of points, as for the magnetic resonance signal $Sw2(L(i))(x(a), y(b), z(c))(t(j))$ in the real-space calculated in the first k-space and real-space transform step, a signal to noise ratio calculating step for calculating a signal to noise ratio $SNR(L(i))(x(a), y(b), z(c))$ at each real-space point of each element coil, from the correction absolute value calculated in the absolute value and phase value calculating step, the noise average value $Na(L(i))(x(a), y(b), z(c))$, and the noise standard deviation $Nd(L(i))(x(a), y(b), z(c))$, calculated in the noise calculating step, a second measurement step for measuring a spectral information of the 2-dimensional k-space or the 3-dimensional k-space $(kx(a), ky(b), kz(c))$, under a water-suppressed condition, a second k-space and real-space transform step for performing a transform between a k-space component and a real-space component, in each k-space axis direction, on a k-space magnetic resonance signal $Sm1(L(i))(kx(a), ky(b), kz(c))(t(j))$ acquired at each element coil in the second measurement step, so as to calculate a magnetic resonance signal in a the 2-dimensional real-space or the 3-dimensional real-space $(x(a), y(b), z(c))$, a phase value correction step for performing a phase correction, where the phase values $\Phi m(L(i))(x(a), y(b), z(c))(t(j))$ of all the points are corrected point-by-point of each real-space point of each element coil, using the correction value calculated in the phase value calculating step above mentioned, on the magnetic resonance signal $Sm2(L(i))(x(a), y(b), z(c))(t(j))$ acquired in the second k-space and real-space transform step so as to calculate a phase corrected magnetic resonance signal $Sm3(L(i))(x(a), y(b), z(c))(t(j))$, a signal to noise ratio multiplying step for multiplying a weighting coefficient calculated with the signal to noise ratio $SNR(L(i))(x(a), y(b), z(c))$ of each real-space point of each element coil in the signal to noise ratio calculating step, to a magnetic resonance signal $Sm3(L(i))(x(a), y(b), z(c))(t(j))$ of each real-space of each element coil calculated in the phase value correction step, a MAC summation step for a complex addition of a magnetic resonance signal $Sm4(L(i))(x(a), y(b), z(c))(t(j))$ of each real-space point of each element coil calculated in the signal to noise ratio multiplying step for each real-space point, so as to make an added signal value $Sm5(x(a), y(b), z(c))(t(j))$ as a magnetic resonance signal value applied the MAC summation, where multiple images obtained by the MAC are added to each other, a time and frequency transform step for performing a transform between a time component and a frequency component in a time-axis direction on a magnetic resonance signal value $Sm5(x(a), y(b), z(c))(t(j))$, which is a signal value of each real-space point of the magnetic resonance signal value after the MAC summation, calculated in the MAC summation step, so as to calculate a magnetic resonance spectroscopic image $Sm6(x(a), y(b), z(c))(f(j))$ of the 2-dimensional real-space or the 3-dimensional real-space-having information in a frequency axis (f-axis) direction.

13. The method for calculating a magnetic resonance spectroscopic image according to claim 12, wherein,
in the noise calculating step, the noise average value $Na(L(i))(x(a), y(b), z(c))$ and the noise standard deviation $Nd(L(i))(x(a), y(b), z(c))$, are calculated using absolute value signals of last M points of the magnetic resonance signal $Sw2(L(i))(x(a), y(b), z(c))(t(j))$ of the real-space calculated in the first k-space and real-space transform step.

14. The method for calculating a magnetic resonance spectroscopic image according to claim 12, further comprising,
a second phase value correction step for performing a phase correction in a spectrum-axis direction on the magnetic resonance spectroscopic image $Sm6(x(a), y(b), z(c))(f(j))$ of the 2-dimensional real-space or the 3-dimensional real-space having an information in a frequency axis (f-axis) direction calculated in the time and frequency transform step, so as to calculate a magnetic resonance spectroscopic image $Sm7(x(a), y(b), z(c))(f(j))$ of the 2-dimensional real-space or the 3-dimensional real-space.

15. The method for calculating a magnetic resonance spectroscopic image according to claims 12, further comprising,
a sensitivity calculating step for calculating a sensitivity distribution of each element coil using the magnetic resonance signal acquired in each element coil in the first measurement step, and further comprising instead of the MAC summation step,
a summation step for performing an operation for correcting an aliasing in an image, using the magnetic resonance signal at each real-space point in each element coil calculated in the phase value correction step and the sensitivity distribution for each element coil calculated in the sensitivity calculating step so as to summed multiple images obtained at each element coil.

* * * * *